(12) United States Patent
Kinugawa et al.

(10) Patent No.: US 8,772,708 B2
(45) Date of Patent: Jul. 8, 2014

(54) TIME-OF-FLIGHT MASS SPECTROMETER

(75) Inventors: Tohru Kinugawa, Osaka (JP); Osamu Furuhashi, Uji (JP)

(73) Assignees: National University Corporation Kobe University, Hyogo (JP); Shimadzu Corporation, Kyoto-Shi (JP)

( * ) Notice: Subject to any disclaimer, the term of this patent is extended or adjusted under 35 U.S.C. 154(b) by 0 days.

(21) Appl. No.: 13/996,372

(22) PCT Filed: Dec. 20, 2011

(86) PCT No.: PCT/JP2011/079471
§ 371 (c)(1),
(2), (4) Date: Nov. 12, 2013

(87) PCT Pub. No.: WO2012/086630
PCT Pub. Date: Jun. 28, 2012

(65) Prior Publication Data
US 2014/0054456 A1  Feb. 27, 2014

(30) Foreign Application Priority Data
Dec. 20, 2010  (JP) ................... 2010-283187

(51) Int. Cl.
*H01J 49/00*  (2006.01)
(52) U.S. Cl.
USPC ......... 250/287; 250/281; 250/282; 250/396 R
(58) Field of Classification Search
CPC ..... H01J 49/40; H01J 49/0027; H01J 49/403; H01J 49/406; H01J 49/0031
USPC .............................. 250/281, 282, 287, 396 R
See application file for complete search history.

(56) References Cited

U.S. PATENT DOCUMENTS

| 4,625,112 A | 11/1986 | Yoshida |
| 5,464,985 A | 11/1995 | Cornish et al. |
| 6,365,892 B1 | 4/2002 | Cotter et al. |

FOREIGN PATENT DOCUMENTS

JP  3797200 B2  7/2006

OTHER PUBLICATIONS

R.J. Cotter, "Time-of-Flight Mass Spectrometry Instrumentation and Applications in Biological Research", American Chemical Society, (1997).
B.A. Mamyrin et al., "The mass-reflectron, a new nonmagnetic time-of-flight mass spectrometer with high resolution", Soviet Physics, JETP 37, 45-48, (1973).

(Continued)

*Primary Examiner* — Michael Maskell
(74) *Attorney, Agent, or Firm* — Bingham McCutchen LLP

(57) ABSTRACT

An embodiment with a dual-stage reflectron is as follows: (1) On the assumption that a reflector has a base potential $X_A(U)$ created by uniform electric fields, its design parameters are adjusted so as to cancel the first and second order derivatives at energy $E=E_0$ of a total time of flight $T(E)$, and a second-order focusing position on a central axis at which the potential value becomes zero is determined (Mamyrin solution). (2) A correcting potential $X_C(U)$ to be superposed on $X_A(U)$, beginning from the second-order focusing position, is calculated so that $T(E)$ of ions reflected in a region deeper than the second-order focusing position will be constant. (3) Voltage values of the reflector electrodes are determined so that a real potential $X_R(U)=X_A(U)+X_C(U)$ is created on the central axis.

20 Claims, 18 Drawing Sheets

(56) References Cited

OTHER PUBLICATIONS

U. Boesl et al., Reflectron time-of-flight mass spectrometry and laser excitation for the analysis of neutrals, ionized molecules and secondary fragments, Int'l Journal of Mass Spectrometry and Ion Processes, 112:121-166, (1992).

Yoshikazu, Yoshida et al., "An improvement of mass spectral resolution of a time-of-flight mass spectrometer by means of a gradient electric field type ion reflector", Journal of the Mass Spectrometry Society of Japan, vol. 36, 2:49-58, (1988).

M.R. Scheifein et al., "Time aberrations of uniform field: an improvement reflectron mass spectrometer for an atom-probe filed-ion microscope", Review of Scientific Instruments, 64:3126-3131, (1993).

L.D. Landau et al., Mechanics Third Editiion vol. 1 Course of Theoretical Physics, Pergamon Press, (1976).

V.M. Doroshenko, et al., "Ideal velocity focusing in a reflection time-of-flight mass spectrometer", Journal of the American Society for Mass Spectrometry, 10:992-999, (1999).

V.M. Doroshenko, Ídeal space focusing in a time-of-flight mass spectrometer an optimization using an analytical approach, European Journal of Mass Spectrometry, 6:491-499, (2000).

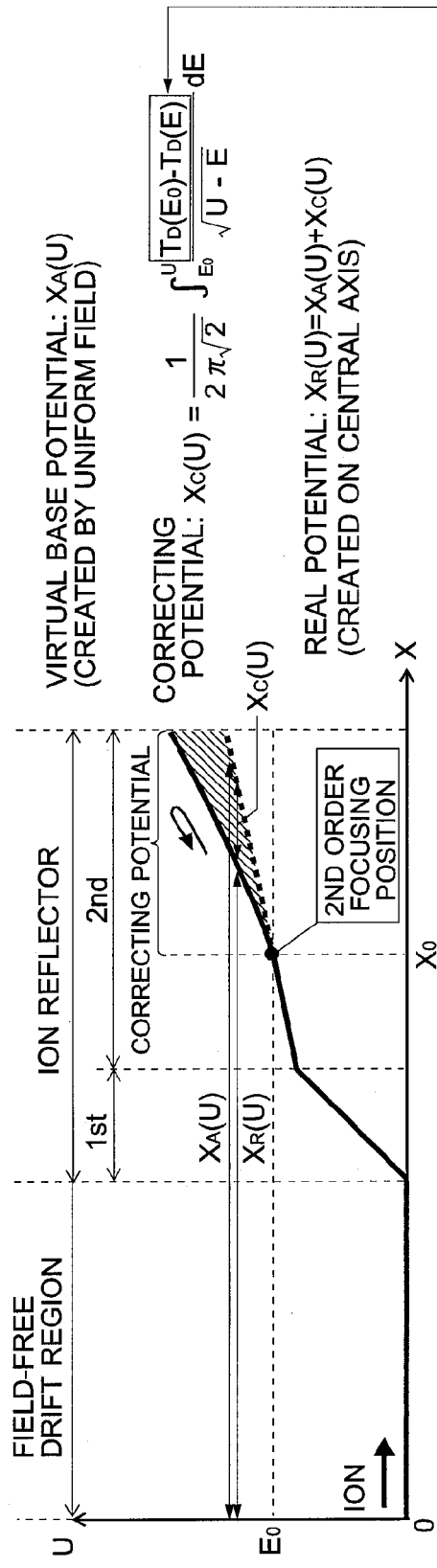
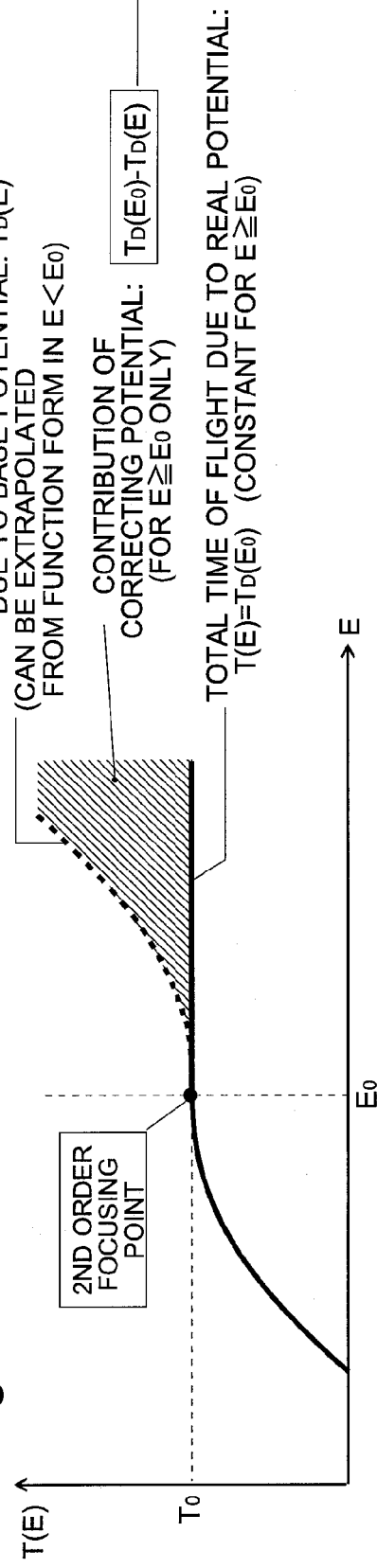
Fig. 10A
Fig. 10B

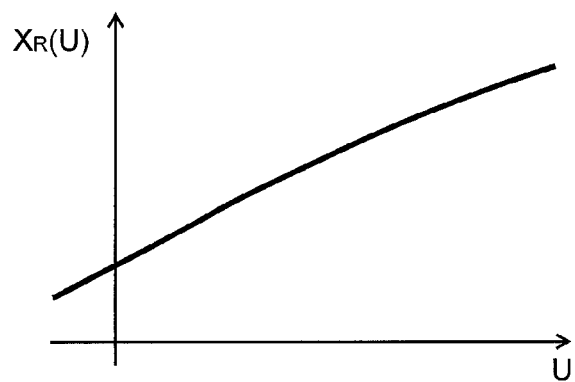
Fig. 25A
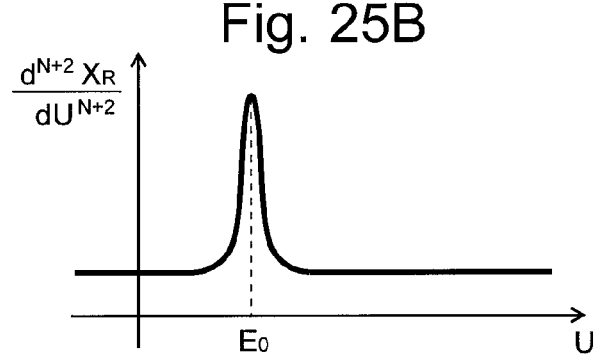
Fig. 25B
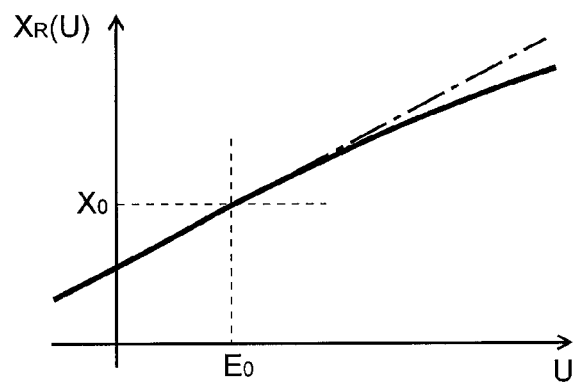

TIME-OF-FLIGHT MASS SPECTROMETER

TECHNICAL FIELD

The present invention relates to a time-of-flight mass spectrometer, and more specifically to a time-of-flight mass spectrometer using an ion reflector.

BACKGROUND ART

In a time-of-flight mass spectrometer (which is hereinafter abbreviated to TOFMS), the time of flight required for ions ejected from an ion source to reach an ion detector is measured, and the mass (or mass-to-charge ratio m/z, to be exact) of each ion is calculated from the time of flight of that ion. One major cause of deterioration in the mass-resolving power is the initial energy distribution of the ions. An initial energy distribution of the ions ejected from the ions source causes a time-of-flight distribution of the ions of the same mass and deteriorates the mass-resolving power. To compensate for the time-of-flight distribution due to the initial energy distribution of the ions, ion reflectors have been widely used. A TOFMS using an ion reflector is hereinafter called the "reflectron" according to the common practice.

An ion reflector has an electric potential increasing in the traveling direction of the ions, and has the function of repelling ions coming through a field-free drift space. An ion having a higher initial energy (initial speed) penetrates deeper into the ion reflector and hence spends a longer period of time flying in the ion reflector when reflected. On the other hand, an ion having a larger amount of initial energy flies at a higher speed and hence spends a shorter period of time flying through the drift space of a fixed length. Therefore, by appropriately adjusting the parameters so as to cancel the increase in the time of flight in the ion reflector by the decrease in the time of flight in the drift space, it is possible to create a state in which the total time of flight from the ion source to the detector is almost independent of the initial energy within a certain range of energy (see Non-Patent Document 1 for details). Such an operation of focusing the same kind of ions with different amounts of kinetic energy on the time-of-flight axis so as to make them simultaneously arrive at the detector is hereinafter called the "energy focusing" according to the common practice.

To date, various types of reflectrons have been developed. They can be roughly divided into two groups: one type is a multi-stage system in which a plurality of regions with a uniform (or nearly uniform) electric field are connected in series, and the other type is a non-uniform electric field system in which the potential continuously changes with the intensity of the electric field defined as a function of the distance. Initially, the multi-stage system is hereinafter described.

The structurally simplest version of the multi-stage system is the single-stage reflectron. A potential of the single-stage reflectron is schematically shown in FIG. 23 (see Non-Patent Document 1). The ion reflector has a uniform electric field (i.e. the potential U is proportional to the distance X). A grid electrode G through which ions can pass is provided at the boundary between the field-free drift region and the ion reflector. In the figure, X=0 is the location of the flight start point and the detection point of the ions, L is the length of the field-free drift space, and a is the penetration depth of the ions into the ion reflector. In this system, if the initial energy of an ion satisfies the following equation (1), the time-of-flight distribution is compensated for up to the first derivative of the energy, and as a result, the first-order energy focusing (which is hereinafter simply called the "first-order focusing") is achieved:

$$L = 2 \cdot a \quad (1)$$

However, in the case of the first-order focusing, since the compensation for the time-of-flight distribution is not achieved for the second and higher-order derivatives of the energy, a high mass-resolving power can be achieved only for ions having a comparatively narrow energy distribution. In the following description, the position corresponding to the depth a in the single-stage reflectron is called the "first-order focusing position."

FIG. 24 is a schematic potential diagram of a dual-stage reflectron. The dual-stage reflectron was developed for the first time by Mamyrin et al. (see Non-Patent Document 2). As shown in FIG. 24, the ion reflector consists of two uniform electric fields, with a grid electrode G provided as a partition at the boundary between the field-free drift region and the first uniform electric field (first stage) as well as at the boundary between the first uniform electric field and the second uniform electric field (second stage). If the first stage is adequately short, and if approximately two thirds of the initial energy is lost in the first stage, the time-of-flight distribution is compensated for up to the second derivative of the energy. That is to say, the second-order energy focusing (which hereinafter is simply called "the second-order focusing") is achieved and a high mass-resolving power is obtained.

According to an analysis by Boesl et al., exact conditions to be satisfied for achieving the second-order focusing in a dual-stage reflectron are given by the following equations (2) (See Non-Patent Document 3. It should be noted that the equations given in the original paper are incorrect; the following equations (2) are the recalculated ones):

$$a = [(c-2b)/2(b+c)] \cdot \{b + [\sqrt{3} \cdot (c-2b)^{3/2}/9\sqrt{c}]\}$$

$$p = 2(b+c)/3c \quad (2)$$

where a is the penetration depth of the ion into the second stage, b is the length of the first stage, c is the length of the field-free drift region, and p is the proportion of the ion energy to be lost in the first stage. Equations (2) suggest that, if the lengths b and c are given, the values of a and p which satisfy the second-order focusing condition can be uniquely determined. In the dual-stage reflectron, since the time-of-flight distribution is compensated for up to the second derivative of the ion energy, a high mass-resolving power can be achieved for ions having a broader energy distribution than in the case of the single-stage reflectron. In the following description, the position corresponding to the depth a in the dual-stage reflectron is called the "second-order focusing position."

As for a multi-stage reflectron, which can be conceived as an extension of the dual-stage reflectron, it can be generally expected that increasing the number of uniform electric fields (or nearly uniform electric fields) in the multi-stage reflectron improves the performance, with the time-of-flight distribution being compensated for up to higher-order derivatives of the ion energy (the cancellation of up to the N-th derivative is hereinafter called the "N-th order focusing"), thus making it possible to achieve a high mass-resolving power for ions having a broader energy distribution. The possibility of improving the performance for an actual increase in the number of stages has been studied by numerical computations in Non-Patent Document 5, which includes a report of the results obtained by correcting the design parameters up to higher-order derivatives without departing from the practically acceptable ranges of the parameters while increasing the number of stages in the ion reflector up to four. However, increasing the number of stages does not lead to a significant increase in the energy range in which a high level of mass-resolving power is obtained. Furthermore, increasing the number of grid electrodes placed on the flight path of the ions causes a greater amount of loss of the ions and deteriorates the sensitivity. Such a system can be said to be practically unusable.

In view of such limits of the multi-stage reflectron, the non-uniform electric field system has been developed as an attempt to reduce the time-of-flight distribution of the ions having an even broader energy distribution. An ideal pinnacle of this system is a reflectron using a simple harmonic motion.

That is to say, as can be understood from the motion of a weight attached to an end of a spring, when the potential U is given by a harmonic function expressed by the following equation (3), the time of flight (TOF) of an ion will be equal to one half of the period of the simple harmonic motion, as given by the following equation (4):

$$U = (1/2) \cdot k \cdot X^2 \quad (3)$$

$$TOF = \pi \sqrt{m/k} \quad (4)$$

where m is the mass of the ion, and k is a constant.

These equations demonstrate that the time of flight is independent of the initial energy, and isochronism is exactly achieved. However, in practice, the absence of the field-free drift region in the potential distribution, as in the case of the harmonic function of equation (3), is a considerably serious drawback for TOFMS, because, without a field-free drift region, the ion source and the detector cannot be placed at any position other than at the bottom of the potential, which imposes an extremely strong restriction on the system design. A technique for solving this drawback is disclosed in Patent Document 1 and Non-Patent Document 4, in which the sum of a potential proportional to the distance X and a potential proportional to the square of the distance X is used as the potential inside the reflector, with the aim of reducing the time-of-flight distribution even in the case where a field-free drift region is connected to an ion reflector having a gradient electric field. This method ensures a certain level of energy-focusing performance over a comparatively broad range of energy. However, it also makes the negative effect of breaking the exact isochronism, thus limiting the improvement of the mass-resolving power.

On the other hand, a configuration of a TOF-TOF system for performing an $MS^2$ analysis is described in Patent Document 2. In this system, a non-uniform electric-field potential is created inside a second ion reflector for the purpose of the energy focusing of the fragment ions produced in a collision cell. In another ion reflector described in Patent Document 4 and Non-Patent Document 7, the entire ion reflector is divided into a decelerating region as the first section and a (non-uniform) correcting potential region as the second section. These documents demonstrate that applying an appropriate non-uniform electric field on the correcting potential region makes the time of flight of ions completely independent of their initial energy (equal to or higher than a specific threshold) over the entire time-of-flight range, i.e. that complete isochronism is theoretically achievable. Specifically, it is shown that an ideal (one-dimensional) potential distribution on the central axis of the correcting potential region can be determined by integral equations. One example is also presented, in which the result of integration is expressed as an analytical function form.

A system which has significantly contributed to the practical realization of a reflectron having both high mass-resolving power and high energy-focusing performance (i.e. high sensitivity) is the system described in Patent Document 3. This system, which can be regarded as a compromise between the multi-stage uniform electric-field system and the non-uniform electric-field system, is a variation of the dual-stage reflectron in which the entire first stage and a portion of the second stage are designed to be a uniform electric-field region using an approximately constant electric field, while the remaining portion extending to the end is designed to be a correcting potential region with a non-uniform electric field adopted therein, whereby the electric-field strength on the central axis is made to substantially increase. To avoid the loss of the ions, no grid electrode is used. The electric-field strength in the first stage is set at a low level so as to improve the ion-beam focusing performance, with a corresponding sacrifice of the mass-resolving power. The amount of correction of the electric-field strength in the second stage is 10% of the uniform electric-field strength or even smaller. However, according to the document, since the equipotential surfaces in the grid-less reflector are not flat but curved, the trajectory of an ion traveling on a path dislocated from the central axis will diverge due to the lens effect. Nevertheless, an advantage still exists in that a higher level of mass-resolving power can be obtained for ions having a broader energy distribution than before, and the system has already been put into practice.

Based on the previously described past improvements of the reflectron, an ideal reflectron is herein defined as "a reflectron capable of the energy focusing up to infinitely high-order terms for a time-of-flight distribution by using a potential distribution created by a non-uniform electric field, at any energy level equal to or higher than a specific level $E_0$." As will be described later, the following five basic conditions must be satisfied for the practical realization of an ideal reflectron.

<1: Complete Isochronism> It should be possible to achieve energy focusing up to infinitely high-order terms with respect to the time of flight.

<2: Suppression of Beam Divergence> A divergence of the beam in the reflector should be suppressed.

<3: Suppression of Off-Axis Aberration> An off-axis aberration, i.e. the temporal aberration for an ion on a path dislocated from the central axis, should be suppressed.

<4: Feasibility of Potential> It should be possible to produce an ideal potential in a practical way, using a limited number of electrodes.

<5: Tolerance for Non-Uniform Electric Field before Correction> As will be described later, it should be possible to realize a practically usable ideal potential even if a non-uniform electric field is present in the vicinity of the beginning portion of the correcting potential before the correction.

The condition <1: Complete Isochronism> can be expressed by the following equation (5):

$$T(E) = T(E_0) + (dT/dE)(E - E_0) + (1/2)(d^2T/dE^2) \cdot (E - E_0)^2 + (1/6)(d^3T/dE^3)(E - E_0)^3 + \ldots \quad (5),$$

where E is the initial energy of the ion, and T(E) is the time of flight of the ion.

A Wiley-McLaren solution, as already described, uses the first-order focusing which cancels the terms of equation (5) up to the first-order differential coefficient by a single-stage reflectron, using a potential created by a uniform electric field. A Mamyrin solution uses the second-order focusing which cancels the terms of equation (5) up to the second-order differential coefficient by a dual-stage reflectron. These solutions cannot be regarded as an ideal reflectron, because the former system leaves the second and higher-order differential coefficients intact, while the latter system leaves the third and higher-order differential coefficients intact.

The conditions <2: Suppression of Beam Divergence> and <3: Suppression of Off-Axis Aberration> are also essential for the practical realization of an ideal reflectron. Both the beam dispersion and the temporal aberration occur due to the fact that $\text{div} E \neq 0$ for a non-uniform electric field in vacuum. Firstly, if the discrepancy from the uniform electric field is large or the curvature of the potential distribution is large, the ion reflector acts as a concave lens, which causes a divergence of the ion trajectory and eventually lowers the signal intensity. Secondly, even if an ideal potential along the central axis is realized, a potential discrepancy inevitably occurs for a trajectory dislocated from the central axis, which causes a temporal aberration and eventually lowers the mass-resolving power. In the following description, the former problem is called the "divergence problem" and the latter is called the "temporal aberration due to the off-axis location."

The condition <4: Feasibility of Potential> is also important from practical points of view, because, even if a correcting potential to be created inside the reflector to achieve complete isochronism has been theoretically determined, that potential cannot always be actually created as a three-dimensional potential distribution. In other words, even if a one-dimensional potential distribution having ideal values on the central axis (which is hereinafter called the "1D-IDL") has been found, it is not guaranteed that a three-dimensional potential distribution which has been simulated based on the 1D-IDL (the simulated distribution is hereinafter called the "3D-SIM") is a practical approximation of the 1D-IDL, because there is the absolute restriction that 3D-SIM should be a solution of the Laplace equation. A strong, specific concern is that an ideal correcting potential has a specific characteristic (which will be described later) at the starting point of the correcting potential, i.e. that the high-order differential coefficients relating to the position of the correcting potential inevitably diverge. As a result, under an electrostatic constraint, the correcting potential can merely be reproduced as an approximation. Accordingly, for the practical realization of an ideal reflectron, it is essential to determine whether a practical isochronism can be achieved by an approximate potential distribution created by a limited number of guard-ring electrodes. In the following description, this determination task is mainly substituted for by the task of initially determining a 1D-IDL, which can be obtained with almost zero numerical discrepancy from ideal values, and then performing numerical calculations on a large scale to obtain a three-dimensional approximate solution 3D-SIM corresponding to that 1D-IDL for a specified set of electrodes.

As will be described later, in the conventional theory for the ideal reflectron, the correcting potential is analytically determined on the premise that the electric field which serves as a base before the correction in the vicinity of the beginning portion of the correcting potential is a uniform electric field. However, a study by the present inventors has revealed that the electric field at the grid electrode placed at the boundary of the electric field is actually disordered due to the seeping of the electric field or other factors, and this disorder fatally deteriorates the isochronism. In the case of a grid-less reflector with no grid electrode, the problem is even more serious because the degree of non-uniformity of the electric field is greater. Accordingly, for the practical realization of an ideal reflectron, the correcting potential must be obtained by using a system as close to a real form as possible. Thus, it is necessary to satisfy the condition <5: Tolerance for Non-Uniform Electric Field before Correction>, which requires that the ideal potential should be applicable even in the case where the electric field which serves as a base in the vicinity of the beginning portion of the correcting potential before the correction is a non-uniform electric field.

Now, let the previously described conventional techniques be evaluated from the viewpoints of the five basic conditions. The <1: Complete Isochronism> has already been achieved, for example, in Patent Document 4 and Non-Patent Document 7 (which are hereinafter called "the documents of Cotter et al.") That is to say, a general solution for the potential distribution of an ideal reflectron capable of the energy focusing up to infinitely high orders has already been obtained in those documents. However, the solution described in those documents is limited to a one-dimensional space (with ions moving on the central axis); there is no mention of how to satisfy the basic conditions relating to three-dimensional motions, such as the conditions <2: Suppression of Beam Divergence> and <3: Suppression of Off-Axis Aberration>. Therefore, no ideal reflectron which can achieve both high mass-resolving power and high sensitivity has yet been practically realized. That is to say, at least either the mass-resolving power or the sensitivity is sacrificed in the currently used reflectrons.

The system described in Patent Document 3 does not exactly satisfy the condition <1: Complete Isochronism>. However, as compared to the reflectrons known by that time, it has achieved a higher level of mass-resolving power for ions with a broader energy distribution. In this respect, the system can be said to be closer to an ideal reflectron. However, a problem exists in that it requires repeating a trial and error process in a computer simulation in order to find a sufficient potential distribution for achieving a required mass-resolving power. It is impractical to use such a trial and error process in order to reach an ideal extremity, i.e. a solution that exactly satisfies the conditions for isochronism. The energy range in which a practical isochronism is achieved is also limited.

The technique described in the documents of Cotter et al. takes the following steps to practically realize an ideal potential:

[Step 1] An ideal potential distribution in the correcting potential region is expressed as a general solution including design parameters (distance and voltage).

[Step 2] The general solution obtained in Step 1 is expanded into a half-integer power series of $(U-E_0)$.

[Step 3] The design parameters are adjusted so that the expansion coefficients obtained in Step 2 will be individually zeroed.

However, taking the aforementioned steps is actually difficult, and in the first place, it is not always evident whether a solution which makes the coefficients in the power series expansion equal to zero actually exists. Furthermore, as already noted, having a general solution of the ideal potential is not enough for practical purposes; it does not make sense if no particular solution which satisfies the conditions <2: Suppression of Beam Divergence> through <5: Tolerance for Non-Uniform Electric Field before Correction> for embodying an ideal reflectron into an actual system is determined. Although Cotter et al. noted the general request that using an ideal one-dimensional potential distribution which has a smaller curvature and is closer to a straight line makes it easier to create an actual system, they proposed no specific technique for achieving that goal. More importantly, even if the method of Cotter et al. is used, it is possible that no practical solution with a small curvature of the potential distribution can be found for some setting of the design parameters. Actually, Cotter et al. mentions no solutions other than the first-order focusing solution, whose existence has already been proved to be evident.

A study by the present inventors has also revealed that, if in the first place there is no position where the N-th order focusing is achieved (this position hereinafter is simply called the "N-th order focusing position"), it is allowed to automatically conclude that there is no practical solution with a small curvature of the potential distribution. The N-th order focusing position can be more specifically defined as follows. Provided that the total time of flight is expressed as a function of energy E, the N-th order focusing position is the position on the central axis at which the potential value is equal to the energy E at which the first through N-th order derivative values are equal to zero. According to the studies on multi-stage reflectrons described in Patent Document 5 and other documents, the N-th order focusing position does not always exist in an arbitrary design; the fact is that there are considerable ranges of design parameters in which no N-th order focusing position can be found. This means that the situation with no N-th order focusing position existing from the start may more frequently occur depending on the setting of the design parameters.

Non-Patent Document 8 (which is hereinafter called the "document of Doroshenko") is a study that succeeded the technique described in the documents of Cotter et al. Similar to Cotter et al., the study is focused on the one-dimensional model. In the documents of Cotter et al., the entire flight path of the ions including the ion source (or ion-accelerating region) is divided into a forward path (upstream region), a return path (downstream region) and a reflector region with a correcting potential, and a generalized integral equation for determining an ideal potential distribution within the reflector region for achieving isochronism for an arbitrary potential distribution on the forward and return paths is presented. On the other hand, in the document of Doroshenko, after an analogy between the reflection of ions by the reflector and the extraction of ions from the ion source is explained, a generalized integral equation for determining an ideal potential distribution inside the ion source for achieving isochronism in the extraction of the ions is described. A particular solution is also discussed, for the reason that using an ideal one-dimensional potential distribution whose curvature is smaller and closer to a straight line makes it easier to realize or design an actual system. In that discussion, on the premise that only a uniform electric field exists in the vicinity of the beginning portion of the correcting potential before the correction, Doroshenko demonstrated that the ideal correcting potential can be expanded into a half-integer power series of $(U-E_0)$, and that the curvature of the correcting potential can be kept small by achieving the first or second-order focusing. However, the premise that "only a uniform electric field exists in the vicinity of the beginning portion of the correcting potential before the correction" contradicts the aforementioned condition <5: Tolerance for Non-Uniform Electric Field before Correction>. In this respect, the problem for the practical realization is not solved at all.

As described thus far, although an ideal one-dimensional potential distribution has been obtained by conventional research and development efforts, no ideal reflectron has yet been realized. This is because no conventional technique can completely satisfy the basic conditions <1: Complete Isochronism> through <5: Tolerance for Non-Uniform Electric Field before Correction>. Practical realization of a three-dimensional, highly feasible, ideal reflectron which completely satisfies the conditions <1: Complete Isochronism> through <5: Tolerance for Non-Uniform Electric Field before Correction> has been strongly demanded for the purpose of improving the performance of mass spectrometers. To provide such a system is one of the major problems in the field of mass spectrometry.

BACKGROUND ART DOCUMENT

Patent Document

Patent Document 1: U.S. Pat. No. 4,625,112
Patent Document 2: U.S. Pat. No. 5,464,985
Patent Document 3: JP-B 3797200
Patent Document 4: U.S. Pat. No. 6,365,892

Non-Patent Document

Non-Patent Document 1: R. J. Cotter, *Time-of-Flight Mass Spectrometry: Instrumentation and Applications in Biological Research*, American Chemical Society, 1997
Non-Patent Document 2: B. A. Mamyrin et al., "The mass-reflectron, a new nonmagnetic time-of-flight mass spectrometer with high resolution", *Soviet Physics*—JETP 37, 1973, pp. 45-48
Non-Patent Document 3: U. Boesl et al., "Reflectron time-of-flight mass spectrometry and laser excitation for the analysis of neutrals, ionized molecules and secondary fragments", *International Journal of Mass Spectrometry and Ion Processes*, 112, 1992, pp. 121-166
Non-Patent Document 4: Yoshikazu Yoshida et al, "An Improvement of Mass Spectral Resolution of a Time-of-Flight Mass Spectrometer by Means of a Gradient Electric Field Type Ion Reflector", *Journal of the Mass Spectrometry Society of Japan*, Vol. 36, No. 2, 1988, pp. 49-58
Non-Patent Document 5: M. R. Scheifein et al., "Time aberrations of uniform field: An improvement reflectron mass spectrometer for an atom-probe filed-ion microscope", *Review of Scientific Instruments*, 64, 1993, pp. 3126-3131
Non-Patent Document 6: L. D. Landau et al., *Mechanics, Third Edition: Volume 1 Course of Theoretical Physics*, Pergamon Press, 1976
Non-Patent Document 7: V. M. Doroshenko et al., "Ideal Velocity Focusing in a Reflectron Time-of-Flight Mass Spectrometer", *Journal of the American Society for Mass Spectrometry*, 10, 1999, pp. 992-999
Non-Patent Document 8: V. M. Doroshenko, "Ideal space focusing in a time-of-flight mass spectrometer: an optimization using an analytical approach", *European Journal of Mass Spectrometry*, 6, 2000, pp. 491-499

SUMMARY OF THE INVENTION

Problem to be Solved by the Invention

The present invention has been developed to solve the previously described problems, and its objective is to provide a reflectron as an ideal pinnacle. Specifically, it is a reflectron that satisfies the following conditions: a discrepancy from the uniform electric field which causes a serious divergence of the ions should not occur; the influence of the off-axis temporal aberration should be suppressed; and a practical isochronism should be achieved for an ion traveling on the central axis. More specifically, the objective of the present invention is to provide a three-dimensional, highly feasible, ideal reflectron which completely satisfies the aforementioned conditions <1: Complete Isochronism> through <5: Tolerance for Non-Uniform Electric Field before Correction>

One problem for the present invention is to obtain a practical potential distribution which achieves isochronism over a wider energy range than the conventional techniques and which has a small curvature of the potential distribution, even in the case where a field-free drift space is present. The reason is because it is most likely that, once such a potential distribution is determined, the work of designing a system and adjusting experimental parameters will be easy. Another problem for the present invention is to provide a reflectron with which isochronism is achieved for the entire mass spectrometric system including the ion source, which is an indispensible component of the mass spectrometer.

Means for Solving the Problems

To solve the aforementioned problems, the present inventors have devised a new technique for obtaining a practical solution which achieves isochronism for any ion exceeding a certain energy level (E=1, details of which will be described later), and which has a small curvature of the potential distribution, regardless of the number of stages in the ion reflector. By the technique adopted in the present invention, it is possible not only to find a general solution of an ideal potential distribution presented in the documents of Cotter et al, but also to determine a particular solution which gives a potential distribution having a sufficiently small curvature for practical application (i.e. which satisfies the conditions <2: Suppression of Beam Divergence> through <5: Tolerance for Non-Uniform Electric Field before Correction>) and which is specific.

Unlike the method described in the documents of Cotter et al., the basic procedure for realizing the present technique takes the following steps:

[Step 1: Setting of Base Potential] A model which approximately achieves isochronism is considered, referring to a multi-stage reflectron such as the Wiley-McLaren solution or the Mamyrin solution. Specifically, the design parameters are adjusted (the first, second or higher-order focusing position is calculated) so that the first, second or higher-order focusing (i.e. $dT/dE=0$, $d^2T/dE^2=0$ and so on) is achieved. The potential distribution $X_A(U)$ of the thus optimized model is the target to be corrected and improved, which is hereinafter called the "base potential".

[Step 2: Superposition of Correcting Potential] An appropriately calculated correcting potential $X_C(U)$ is superposed on the base potential $X_A(U)$ set in Step 1 so as to obtain a resultant potential $X_R(U)=X_A(U)+X_C(U)$ which satisfies the condition <1: Complete Isochronism>. This resultant potential $X_R(U)$ is the very potential which should be actually realized on the central axis. This potential is hereinafter called the "real potential". The position at which the superposition of the correcting potential begins is the first-order focusing position in the Wiley-McLaren solution, the second-order focusing position in the Mamyrin solution, and the like. The correcting potential $X_C(U)$ is superposed on the region deeper than this point inside the reflector.

In Step 1, an optimized correcting potential $X_C(U)$ is determined from a generally known fact (that it is possible to make the first or second derivative equal to zero by using only uniform electric fields, and to uniquely determine the first or second-order focusing position). As will be described later, this step guarantees that a practically usable particular solution with a small curvature of the potential distribution can be obtained under given constraints. This technique is based on the completely new technical idea that lower-order terms (such as the first and second terms) in equation (5) are initially cancelled beforehand by the Wiley-McLaren or Mamyrin solution, after which the remaining higher-order terms are cancelled by the correcting potential. By this method, since the contributions of the lower-order terms in the vicinity of the starting point of the correcting potential are eliminated in advance of the correction, no significant discrepancy of the potential will occur. In other words, the electric fields before and after the position at which the correction begins in the ion reflector will be smoothly connected to each other. (To be exact, this means that the differential coefficients relating to the position will be continuous up to a considerably high order, thus guaranteeing a practically sufficient level of smoothness. Naturally, they will not be continuous up to infinitely high orders.) Such a smooth connection of the electric fields enhances the degree of <4: Feasibility of Potential>. As a result, both the beam divergence at the starting point of the correcting potential and the temporal aberration due to the off-axis location are suppressed.

However, in a more realistic system, due to the influences of the seeping of the electric field through the grid electrode provided at the boundary of the electric fields, or other factors, it is difficult to avoid the deterioration of isochronism by the previously described Steps 1 and 2, which are premised on the use of uniform electric fields as the base potential, as well as by the method described in the document of Doroshenko. In the case of a grid-less reflector which uses no grid electrode, the problem is even more serious since the degree of non-uniformity of the electric field is higher. Accordingly, in one improved version of the previously described technique, the condition that a single-stage reflector or a multi-stage reflector with two or more stages should be composed of only uniform electric fields is removed, so that a reflector including a non-uniform electric field may also be included. Under this condition, the base potential $X_A(U)$ will not always be a potential created by uniform electric fields. Even in that case, the starting point of the superposition of the correcting potential is set at the N-th order focusing position newly obtained by a numerical calculation or similar method.

The time-of-flight mass spectrometer according to the present invention uses an ideal potential distribution obtained by the previously described new technique. Specifically, it is a time-of-flight mass spectrometer including an ion ejector for accelerating target ions by imparting a certain amount of energy to the ions, an ion reflector for reflecting ions ejected from the ion ejector and turning the ions around by an effect of an electric field, an ion detector for detecting the ions reflected by and exiting from the ion reflector, and a reflector driver for driving the ion reflector so as to create a reflecting electric field inside the ion reflector, wherein:

with X denoting a coordinate along a central axis of the ion reflector, the reflector driver applies a voltage to the ion reflector so as to create, inside an inner hollow area of the ion reflector and along the central axis of the ion reflector, a predetermined potential distribution $U_A(X)$ in which the potential monotonously changes over the entire ion reflector and therefore an inverse function $X_A(U)$ can be uniquely obtained, thus creating an N-th order focusing position at a position with coordinate $X_0$ and potential $E_0$ inside the ion reflector; and the reflector driver also applies a voltage to the ion reflector within a space having the N-th order focusing position with coordinate $X_0$ as a starting point and extending into a deeper region, so as to superpose, on the predetermined potential $X_A(U)$, a predetermined correcting potential $X_C(U)$ which can be approximated by a formula proportional to $\{U(X)-E_0\}^{N+3/2}$ in the vicinity of the coordinate $X_0$ and which is expressed as a smooth function continuing from the coordinate $X_0$ into the deeper region.

In one mode of the time-of-flight mass spectrometer according to the present invention, a forward ion drift region for making the ions ejected from the ion ejector fly forward is provided between the ion ejector and the ion reflector, the ion reflector subsequently reflects the ions passing through the forward ion drift region and turns the ions around by the effect of the electric field, and a backward ion drift region for making the ions reflected by and exiting from the ion reflector fly in a direction opposite to the forward ion drift region is provided between the ion reflector and the ion detector. These ion drift regions may be field-free drift regions for making the ions fly freely.

The forward ion drift region and the backward ion drift region are not indispensible; it is possible to adopt the configuration in which the ion ejector and the ion reflector, as well as the ion reflector and the ion detector, are connected to each other with no drift region or similar space provided in between.

In the time-of-flight mass spectrometer according to the present invention, the electric field which is to be the predetermined potential distribution $X_A(U)$ may be a uniform electric field at least in the vicinity of the coordinate $X_0$. Naturally, the electric field may be a uniform electric field not only in the vicinity of the coordinate $X_0$ but also over the entire ion reflector.

In the time-of-flight mass spectrometer according to the present invention, a grid electrode may be provided inside the inner hollow area of the ion reflector, the grid electrode dividing the ion reflector into a plurality of stages. In this configuration, the ion reflector operates as a single-stage ion reflector or a multi-stage ion reflector with two or more stages. It is also possible to adopt a grid-less structure with no grid electrode provided inside the inner hollow area of the ion reflector.

In the configuration using the grid electrode in the aforementioned manner, although the stages are separated by the grid electrode, the seeping of the electric field through the openings of the grid electrode is unavoidable. Therefore, the electric field will not be a uniform electric field (i.e. it will be a non-uniform electric field) at least in the vicinity of the boundary. The degree of non-uniformity of the electric field will be even more noticeable in the case where a multi-stage system is to be realized in a grid-less structure. However, in the time-of-flight mass spectrometer according to the present invention, the predetermined potential distribution $X_A(U)$ may be created by a non-uniform electric field.

In the time-of-flight mass spectrometer according to the present invention, there is theoretically no upper limit of the value of N. However, in practice, increasing the value of N makes it more difficult to calculate the N-th order focusing position. To avoid this situation, and in respect of the cancellation of higher-order terms by the correcting potential, N may be as small as one or two, which is sufficient for practical purposes.

Accordingly, in one preferable mode of the present invention, the ion reflector is a single-stage system, a first-order focusing position inside the ion reflector is selected as the starting point, and a correcting potential for N=1, which is proportional to $\{U(X)-E_0\}^{2.5}$, is superposed on a region in the vicinity of the boundary of the starting point.

In another preferable mode of the present invention, the ion reflector is a dual-stage system, a second-order focusing position inside the ion reflector is selected as the starting point, and a correcting potential for N=2, which is proportional to $\{U(X)-E_0\}^{3.5}$, is superposed on a region in the vicinity of the boundary of the starting point.

Even when the ion reflector is a dual-stage system, it is possible, as in the case of the single-stage system, to select a first-order focusing position inside the ion reflector as the starting point and superpose a correcting potential for N=1, which is proportional to $\{U(X)-E_0\}^{2.5}$, on a region in the vicinity of the boundary of the starting point.

In the time-of-flight mass spectrometer according to the present invention, the ion ejector can be constructed in various forms, such as an orthogonal acceleration ion source or MALDI (matrix-assisted laser desorption/ionization) ion source.

In the time-of-flight mass spectrometer according to the present invention, an aperture or slit for limiting the passing area of the ions may be provided between the ion ejector and the reflector in order to suppress an influence from the off-axis aberration. Alternatively, it is also possible to provide the ion ejector or a portion of the electrodes of the reflector with the function of limiting the passing area.

In the case where the forward ion drift region and the backward ion drift region are provided in the time-of-flight mass spectrometer according to the present invention, such ion drift regions, in most cases, have no electric fields. However, it is possible to provide an accelerating or decelerating region in a portion of the ion drift regions. A focusing lens for suppressing the influence of the off-axis aberration may be set in a portion of the forward ion drift region, or the ion ejector may be provided with the effect of a focusing lens.

In the time-of-flight mass spectrometer according to the present invention, the ion reflector can also be constructed in various forms. Typically, the ion reflector may include a plurality of thin electrodes arranged along an ion beam axis. In this case, the reflector driver can be constructed as a voltage source for applying a predetermined direct-current voltage to each of the plurality of thin electrodes individually. Another example is a system in which the plurality of thin electrodes are individually connected to each resistor included in a resistor network, with a predetermined voltage applied between the two ends of the resistor network so that an appropriate fraction of the voltage is applied to one of the thin electrodes.

The ion reflector may include a resistance element having an electric resistance adjusted along the ion beam axis. If such a resistance element is used, the potential can be continuously changed along the ion beam axis, so that a more ideal potential can be formed than in the case of using a plurality of thin electrodes. Alternatively, the ion reflector may be created using a printed board or a substrate produced by a high-precision microfabrication technique. If a plurality of electrodes are formed on a printed board or microfabricated substrate by etching or other processes, a higher level of precision in the position of the electrodes can be achieved at a lower cost than in the case of using a plurality of thin electrodes. The processing accuracy can be as high as several tens of micrometers for printed boards, and a few micrometers to submicron levels for microfabricated substrates.

The time-of-flight mass spectrometer according to the present invention is not limited to a TOFMS having a single ion reflector; it may be designed as a multi-reflection time-of-flight mass spectrometer including a plurality of ion reflectors arranged opposite to each other so that ions are reflected a plurality of times between the plurality of ion reflectors, with at least one of the plurality of ion reflectors being the aforementioned ion reflector in which a predetermined correcting potential $X_C(U)$ is superposed on the predetermined potential $X_A(U)$. This design can provide an extremely long flight distance, and therefore, is particularly effective for improving the mass-resolving power.

Effect of the Invention

With the time-of-flight mass spectrometer according to the present invention, a high level of energy-focusing performance can be achieved for ions with a broader energy distribution than before by using a truly ideal reflectron which could not be conventionally realized. Therefore, for example, even if the ions at the point of ejection are broadly distributed over a large space within an ion source (ion ejector) and there is a significant variation in the amount of energy imparted to them, a high level of mass-resolving power is achieved. The divergence of the ions inside the ion reflector is also prevented, as a result of which the detection sensitivity of the ions is also improved. Thus, a reflectron having both high mass-resolving power and high sensitivity can be provided, overcoming the restriction for the conventional reflector-type TOFMSs that there is a trade-off between the mass-resolving power and the sensitivity. Since an ideal extremity of the potential distribution is uniquely determined, the difficult task of adjusting the system parameters by a complicated process is no longer necessary, and therefore, the cost of the system design can be lowered. Furthermore, the high energy-focusing performance means that the position of the TOF peaks will not be affected by a change in the initial energy of the ions, which significantly contributes to an enhancement of the mass accuracy.

BRIEF DESCRIPTION OF THE DRAWINGS

FIG. 10A is a conceptual diagram showing a relationship between the base potential and the real potential in the system shown in FIG. 7, and FIG. 10B is a conceptual diagram showing the contributions of the base potential and the real potential to the entire time of flight.

FIGS. 25A and 25B are graphs showing a method for distinguishing between the base potential and the correcting potential.

BEST MODE FOR CARRYING OUT THE INVENTION

[Verification with Ideal System]

Initially, a detailed description is given about the case where the method for designing a potential in an ion reflector characteristic of the TOFMS according to the present invention is applied in an ideal system. An ideal system in the following description is a situation as follows:

(1) The ion source (ion ejector) is not included as a component of the system; ions which have begun their flight from a certain point inside the field-free drift region with different amounts of initial energy are reflected by the reflector and arrive at the detector.

(2) In a simulation, an ideal grid electrode is used which causes neither the seeping of the electric fields nor the deflection of ions at the grid electrode partitioning the electric fields.

(3) The guard-ring electrodes used in the simulation (with an electrode thickness of 0.2 mm) have a circular opening (with an inner diameter of 40 mm) and are arranged at intervals of 5 mm, with no upper limit of the number of the electrodes.

(4) The electric field inside the ion reflector is a uniform electric field.

A method for designing an ion reflector of the TOFMS according to the present invention is hereinafter described along two specific examples, i.e. a single-stage reflectron and a dial-stage reflectron.

[The Case of Single-Stage Reflectron]

Figure 1:
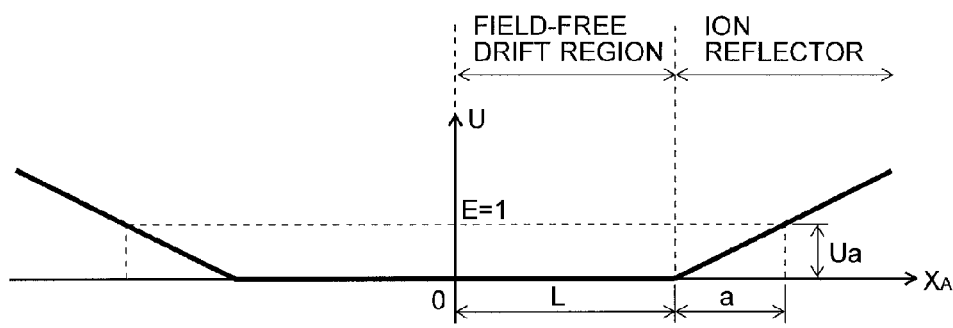
FIG. 1 is a schematic profile of a base potential to be used as a basis for determining an ideal form of the real potential for a single-stage reflectron.
Figure 23:
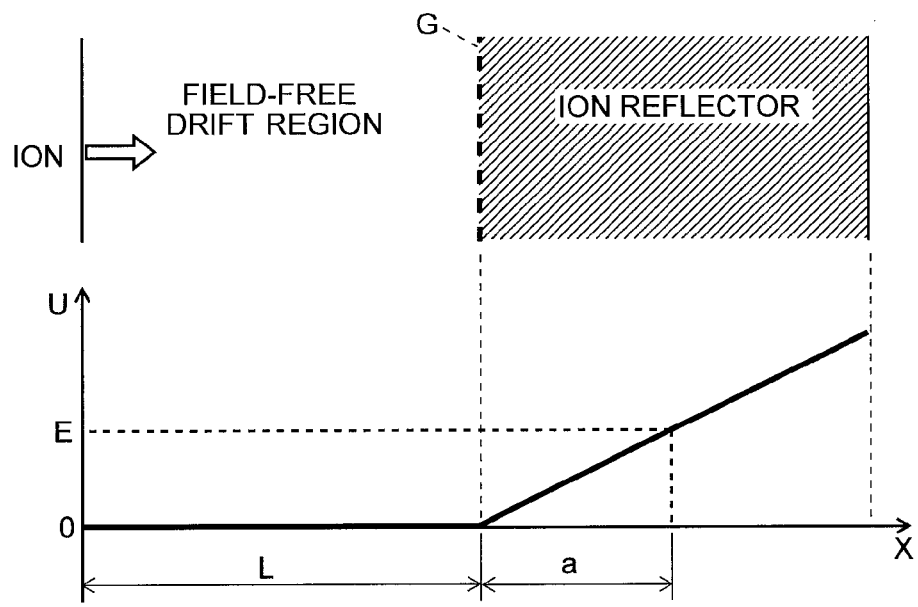
FIG. 23 is a schematic potential chart of a commonly used single-stage reflectron.

A method for calculating the base potential $X_A(U)$ and the correcting potential $X_C(U)$ for a model of a single-stage reflectron having a single uniform electric field is hereinafter described in detail. For the sake of a discussion to be made later, a base potential $X_A(U)$ as shown in FIG. 1, which is obtained by making the potential distribution shown in FIG. 23 laterally symmetrical with respect to the coordinate origin X=0, is assumed, and a periodic motion of an ion in this potential distribution is imagined. (In the present description, U is the potential value, X* is the coordinate along the central axis, and "*" is an arbitrary subscript for distinction. According to this notation, X*(U) normally means the inverse function of the potential distribution. However, this inverse function X*(U) is also simply called the potential in the following description.) Specifically, the base potential $X_A(U)$ is expressed as the following linear equation (6) representing a uniform electric field:

$$X_A(U)=L+(a/U_a)U \tag{6}$$

It should be noted that this equation (6) is valid only for $X_A(U) \geq 0$; the potential for $X_A(U) < 0$ can be obviously determined because of the lateral symmetry.

If the mass and energy of an ion is denoted by m and E, respectively, the initial velocity of the ion at X=0 is $\sqrt{2E/m}$. Accordingly, the time of flight $T_S(E)$ for one turn in the single-stage system is given by the following equation (7-1):

$$T_S(E)=4\{[L/\sqrt{2E/m}]+(a/U_a)\sqrt{2mE}\} \tag{7-1}$$

Figure 2:
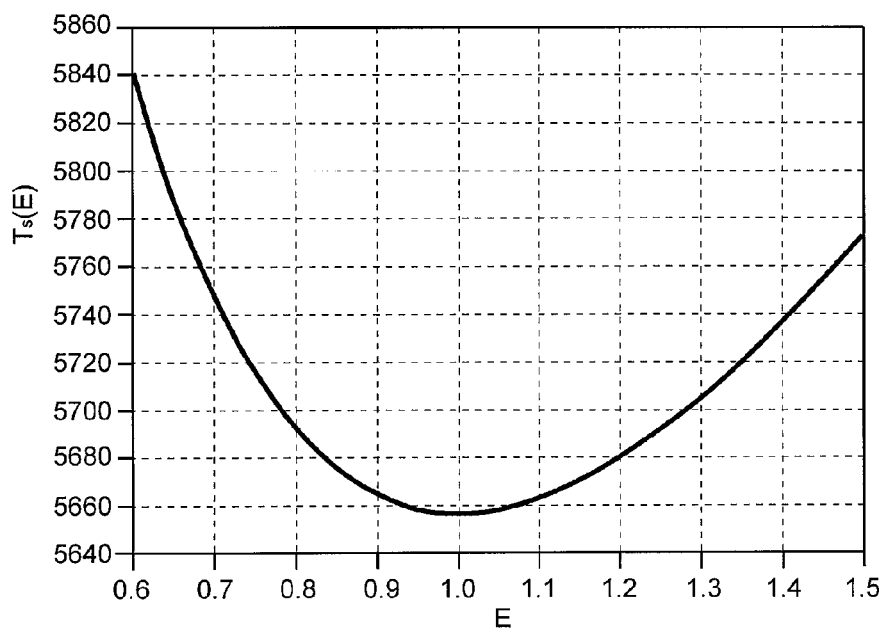
FIG. 2 is a graph showing a relationship between the energy E and the time of flight $T_S(E)$ for one turn when L=1,000 mm in the system shown in FIG. 1.

Using mass m=1 and energy $U_a=1$ as the reference values, equation (7-1) can be simplified as follows:

$$T_S(E)=4(T_{free}(E)+T_{ref-a}(E)) \tag{7-2}$$

$$T_{free}(E)=L/\sqrt{2E} \tag{7-3}$$

$$T_{ref-a}(E)=a\sqrt{2E} \tag{7-4}$$

where $T_{free}(E)$ is the period of time required for the ion to pass through the field-free drift region, and $T_{ref-a}(E)$ is the period of time required for the ion to fly in the uniform electric field inside the ion reflector. When the first-order focusing condition is satisfied, i.e. when $(dT_S/dE)_{E=1}=0$, the well-known aforementioned equation (1) is obtained. As a calculation example, a relationship between the energy E and the time of flight $T_S(E)$ for one turn for L=1,000 mm is shown in FIG. 2. When the energy E=1, the first-order differential coefficient is zero ($T_S(E)$ is at a minimum), which confirms that the first-order correction (the cancellation of the first term in equation (5)) is achieved. The solution thus obtained is none other than the Wiley-McLaren solution, one of the conventional techniques.

In the technique adopted in the present invention, a correcting potential is superposed on the base potential $X_A(U)$ created by the uniform electric field expressed by equation (6) in order to find a solution for achieving complete isochronism. Ideally, it is expected that a solution which satisfies the following conditions is the best solution: in FIG. 2, the time of flight $T_S(E)$ for one turn within the range of $E \geq 1$ is $T_S(E)=T_S(1)$ (constant), the time of flight $T_S(E)$ for one turn is smoothly connected at the boundary between $E<1$ and $E \geq 1$, and a complete energy isochronism is achieved in the correcting potential region for $E \geq 1$ (with a non-uniform electric field superposed thereon). As for the potential distribution, the best case scenario is that isochronism is achieved by simply adding, within the range of $|X| \geq (L+a)$, a slight correcting potential $X_C(U)$ to the potential $X_A(U)$ created by the uniform electric field, and that the eventually obtained real potential $X_R(U)=X_A(U)+X_C(U)$ is also smoothly connected at $X_R=L+a$. In practice, a solution which satisfies such an ideal extremity can be uniquely obtained, as will be described hereinafter.

Non-Patent Document 6 discloses a method by which the aforementioned real potential $X_R(U)$ (i.e. the inverse function of a potential distribution U(X) which yields the given time of flight) can be calculated back from an arbitrary time of flight T(E) for one turn. The following equation (8) is an equation originally presented as equation (12.2) in Non-Patent Document 6:

$$X_R(U) = \frac{1}{2\pi\sqrt{2m}} \int_0^U \frac{T(E)\,dE}{\sqrt{U-E}} \tag{8}$$

In the present case, equation (8) can be rewritten as the following equation (9-1):

$$\begin{aligned} X_R(U) &= \frac{1}{2\pi\sqrt{2}} \int_0^U \frac{T(E)\,dE}{\sqrt{U-E}} \\ &= \frac{1}{2\pi\sqrt{2}} \left[ \int_0^1 \frac{T_S(E)\,dE}{\sqrt{U-E}} + \int_1^U \frac{T_S(1)\,dE}{\sqrt{U-E}} \right] \\ &= \frac{1}{2\pi\sqrt{2}} \left[ \int_0^U \frac{T_S(E)\,dE}{\sqrt{U-E}} + \int_1^U \frac{(T_S(1)-T_S(E))\,dE}{\sqrt{U-E}} \right] \\ &= X_A(U) + X_C(U) \end{aligned} \tag{9-1}$$

This equation demonstrates that an ideal potential distribution can be uniquely determined by integral calculations.

It should be noted that the base potential $X_A(U)$ created by the uniform electric field and the correcting potential $X_C(U)$ are respectively given by the following equations (9-2) and (9-3):

$$X_A(U) = \frac{1}{2\pi\sqrt{2}} \int_0^U \frac{T_S(E)}{\sqrt{U-E}}\,dE \tag{9-2}$$

$$X_C(U) = \frac{1}{2\pi\sqrt{2}} \int_1^U \frac{T_S(1)-T_S(E)}{\sqrt{U-E}}\,dE \tag{9-3}$$

Equation (9-2) represents the potential distribution which will be obtained if $T_S(E)$ has been extended into the energy region higher than E=1. Accordingly, the base potential $X_A(U)$ created by the uniform electric field on the lower-energy side (the region before the first-order focusing position) will be extended into U>1. As a result, the discrepancy from the uniform electric potential will be entirely put together in the correcting potential $X_C(U)$. Under this condition, a complete isochronism solution which minimizes the discrepancy from the uniform electric field which is practically important can be restated as a complete isochronism solution which maintains the correcting potential $X_C(U)$ as small as possible. If this condition is not satisfied, the trajectory of the ions will be diverged due to the lens effect. Although the importance of such a solution was already pointed out in the document of Cotter et al., the necessary and sufficient condition for assuredly maintaining the correcting potential $X_C(U)$ at small values has not yet been found.

On the other hand, equation (9-3), which has been derived by the present inventors, shows that the correcting potential $X_C(U)$ can be maintained at small values by reducing the value of $T_S(1)-T_S(E)$ included in the integral. By this fact, as initially expected, the idea of choosing $T_S(E)=T_S(1)$ (constant) as the time of flight for one turn within the range of $E \geq 1$ is once more justified. This finding also suggests a non-obvious contact point between the multi-stage reflectron using uniform electric fields and a reflectron using a non-uniform electric field. That is to say, in the Taylor expansion equation shown in equation (9-4), it is possible to adopt the method of sequentially zeroing the differential coefficients on the right side, from lower to higher orders, so as to maintain the correcting potential $X_C(U)$ at small values.

$$T_S(1)-T_S(E)=-(dT_S/dE)_{E=1}(E-1)-\{1(2!)\}(d^2T_S/dE^2)_{E=1}(E-1)^2- \ldots -\{1/(n!)\}(d^nT_S/dE^n)_{E=1}(E-1)^n \quad (9\text{-}4)$$

The presence of such a solution is guaranteed by Non-Patent Document 5.

Figure 3A:
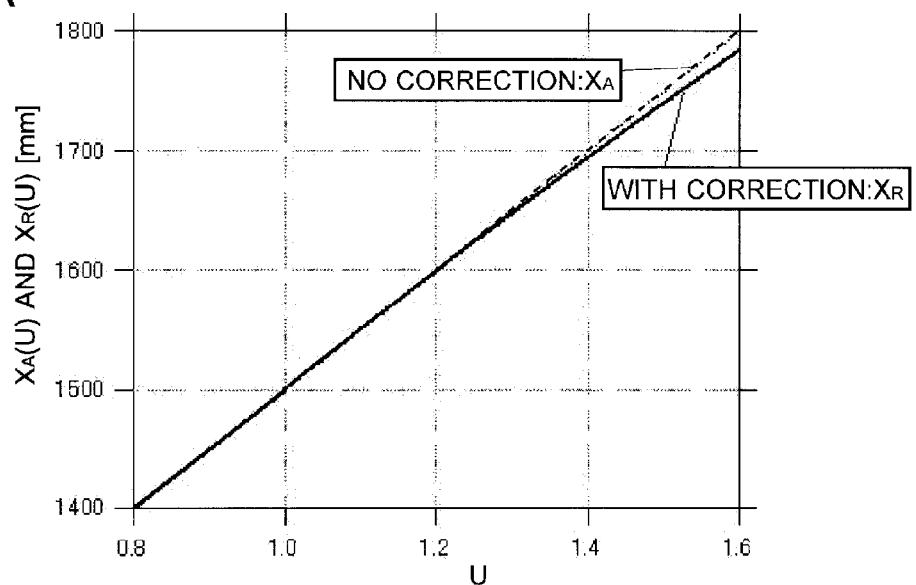
FIG. 3A is a graph showing a calculation result (1D-IDL) of the real potential $X_R(U)$ and the base potential $X_A(U)$ in the system shown in FIG. 1.
Figure 3B:
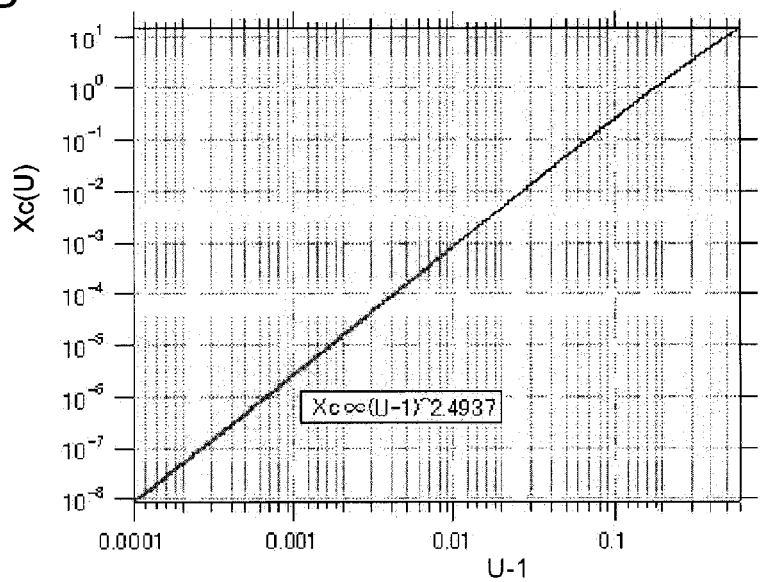
FIG. 3B is a graph showing a calculation result (1D-IDL) of the correcting potential $X_C(U)$.

Specifically, in the case of the single-stage reflectron, $T_S(1)-T_S(E)$ on the right side of equation (9-3) can be reduced to an extremely small, second-order quantity for the energy difference $(E-1)$ in the vicinity of $E=1$ by imposing the first-order focusing condition $(dT_S/dE)_{E=1}=0$. As a result, the correcting potential $X_C(U)$ will also be extremely small, so that $X_C(U=1)=0$. A calculation result (1D-IDL) of the real potential $X_R(U)$ is shown in FIG. 3A. The potential for $U \leq 1$ is the same as the base potential $X_A(U)$ created by the uniform electric field, while the potential for $U>1$ is composed of the base potential $X_A(U)$ of the uniform electric field of the same strength with an extremely small correcting potential $X_C(U)$ added thereto. As can be understood from the 1D-IDL result shown in FIG. 3A, the real potential $X_R(U)$ is smoothly connected at $U=1$ (which corresponds to $X_R(1)=L+a=1500$), and the correcting potential $X_C(U)$ is much smaller than the base potential $X_A(U)$ created by the uniform electric field. Therefore, it is expected that the correcting potential $X_C(U)$ can be realized with a practical level of accuracy by applying an appropriate voltage to each of the grid-less guard-ring electrodes. Since the absolute value of the correcting potential is small, it is expected that no significant divergence of ions will occur. FIG. 3B is a double logarithmic graph (1D-IDL) of the correcting potential $X_C(U)$ plotted against U-1, which shows that the correcting potential in the present case lies on an approximately straight line, maintaining the relationship of $X_C(U) \propto (U-1)^{2.5}$ within a range where U-1 is small.

Using the corrected real potential $X_R(U)$ obtained in the previously described manner, the relative value $\delta T/T$ of the discrepancy of the time of flight has been calculated for an ion which begins flying from the coordinate X=0 in the positive direction of the X axis (rightward in FIG. 1) and which is then reflected by the ion reflector and arrives at the detector placed at the coordinate X=0. The time of flight TOF(E) can be calculated by the following equation (10):

$$TOF(E) = 2\int_0^{X_E} \frac{dX}{v} \quad (10)$$
$$= 2\int_0^{X_E} \frac{dX}{\sqrt{2(E-U(X))}}$$
$$= 2\left[\int_0^L \frac{dX}{\sqrt{2E}} + \int_L^{L+a} \frac{dX}{\sqrt{2(E-U_1(X))}} + \int_{L+a}^{X_E} \frac{dX}{\sqrt{2(E-U_2(X))}}\right]$$

where $X_E$ is the X coordinate of the turn-around point (position) of the ion, and $U_1(X)$ and $U_2(X)$ are potential distributions within the ranges of $L \leq X \leq L+a$ and $X \geq L+a$, respectively.

Figure 4:
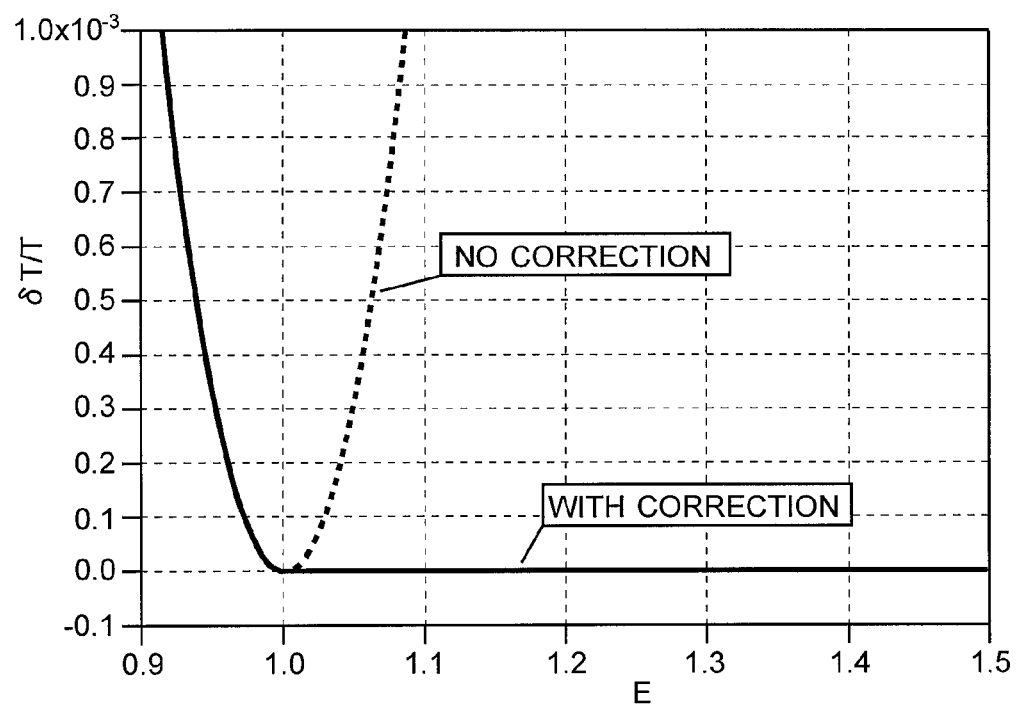
FIG. 4 is a graph showing a calculation result (1D-IDL) of the relationship between the relative value δT/T of the discrepancy of the time of flight and the initial energy in the system shown in FIG. 1.

FIG. 4 shows the calculation results (1D-IDL) for the cases with or without the correcting potential. Without the correcting potential (i.e. in the case of the conventional technique of Wiley McLaren solution), the range within which the discrepancy of the time of flight is small is considerably narrow; the energy range where $\delta T/T \leq 10^{-4}$ is achieved is no greater than $\pm 3\%$. This means that, if the energy is spread to $\pm 3\%$, the mass-resolving power RS, given by $RS=T/(2\delta T)$, will be as low as 5,000. By contrast, in the case where the correcting potential $X_C(U)$ is added, a considerably exact isochronism is achieved within the range of $E \geq 1$. Although the graph shows a limited range of $E \leq 1.5$, it can still be confirmed that $E=1.25 \pm 0.25$, i.e. that a complete energy focusing can be achieved (on the central axis) over a broad energy range of $\pm 20\%$ of the initial energy. Naturally, the energy focusing is also exactly achieved in the case of $E \geq 1.5$. Therefore, the energy focusing of ions having an even broader energy distribution can be completely achieved by increasing the length of the ion reflector as needed.

The largest difference between the graphs with or without correction in FIG. 4 is whether or not the lower and higher energy sections of the curve are symmetrical with respect to the boundary line of E=1. The result (1D-IDL) without correction is in the form of an even function similar to a parabolic curve symmetrical with respect to the line E=1, whereas the symmetry is completely broken in the case of the graph with correction. Such a disappearance of symmetry cannot occur in a multi-stage reflectron; to realize such a state, it is necessary to add a correcting potential that cannot be extended into the lower-energy region (U<1), as in the case of $X_C(U) \propto (U-1)^{2.5}$. In other words, a half-integer power is indispensible for creating such an asymmetrical state.

Thus, an ideal potential distribution of the reflector for achieving isochronism has been theoretically obtained. However, the obtained function form inevitably causes a divergence of the higher-order differential coefficients relating to the position because, as stated earlier, the correcting potential $X_C(U)$ in the vicinity of the starting point of the correcting potential is approximated by a half-integer power (2.5). Therefore, it is impossible to exactly realize it as a potential distribution in a vacuum atmosphere. Furthermore, since the starting point of the correcting potential is a point where all the ions with $E \geq 1$ pass through, it is necessary to quantitatively grasp its influence. In view of these problems, a verification simulation (3D-SIM) has been performed to determine whether a practical isochronism can be achieved even by an approximate potential distribution created by a limited number of guard-ring electrodes. Hereinafter, the result of a simulation for a single-stage reflectron is initially described, followed by the description of the result of a simulation for a dual-stage reflectron. For definite comparison between the two cases, the system parameters were adjusted so that the uniform electric field serving as the base at the starting point of the correcting potential would have the same strength in both simulations.

In the present simulation, L=829.123 mm and a=L/2=414.5615 mm. The total length of the reflectron was 670 mm. The guard-ring electrodes had 134 plate electrodes arranged at intervals of 5 mm, with each plate electrode measuring 40 mm in inner diameter and 0.2 mm in thickness. In this system, the potential is corrected within the range of equal to or higher than 5600 V so as to enable the energy focusing of the ions with an energy distribution of 7 keV±20%. An appropriate voltage was applied to each of the guard-ring electrodes so as to create an ideal form of the real potential on the central axis of the reflectron.

Figure 5A:
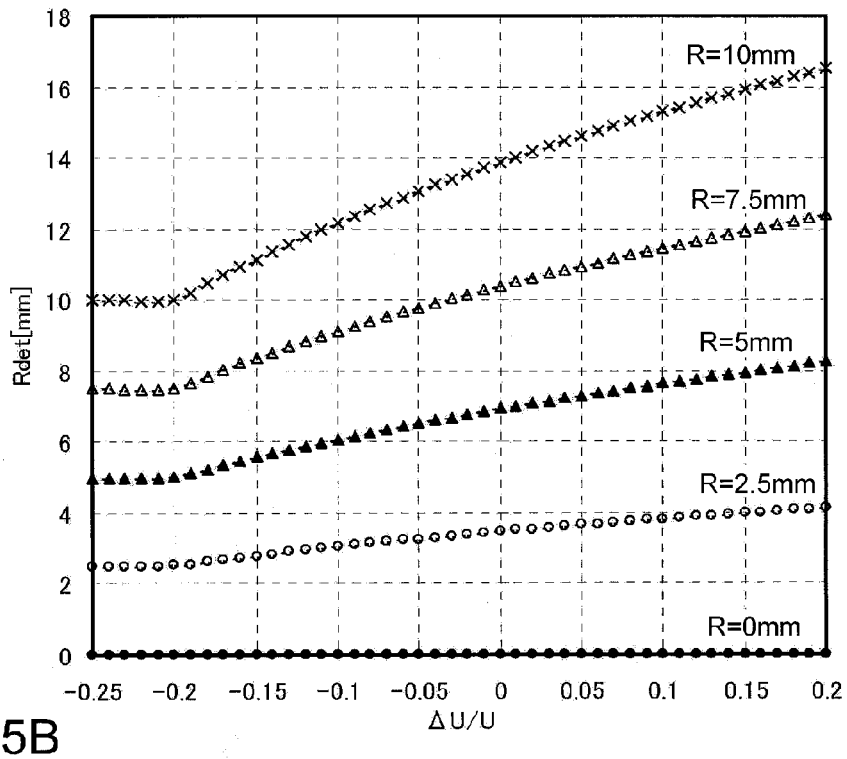
FIG. 5A is a graph showing a calculation result of the relationship between the displacement Rdet from the central axis of the ions which arrived at a detector and the relative energy distribution ΔU/U.
Figure 5B:
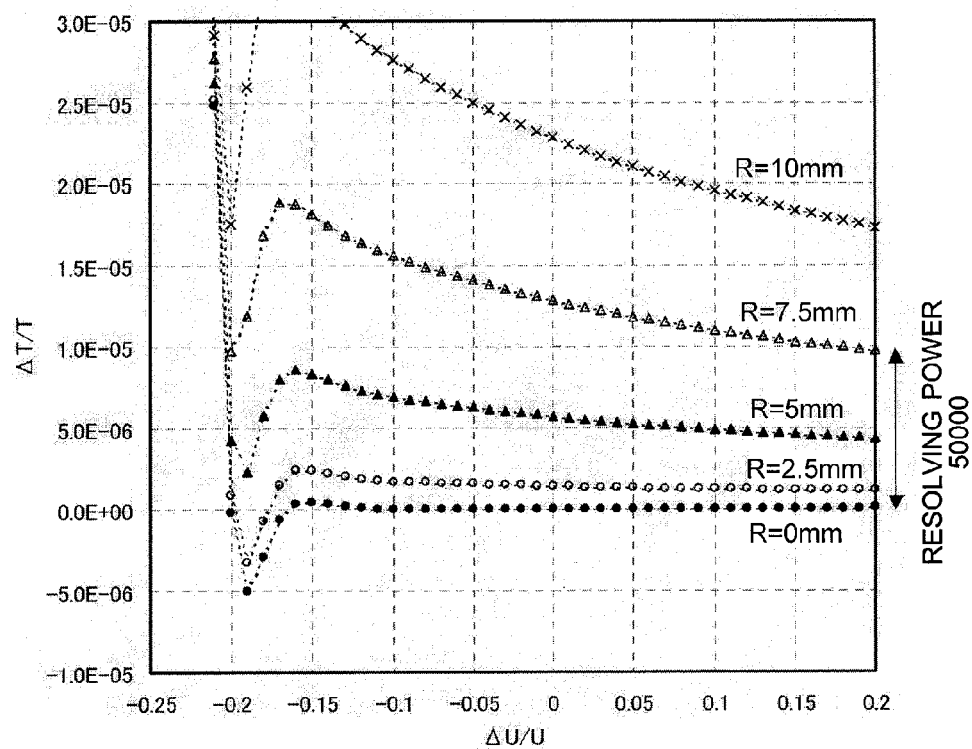
FIG. 5B is a graph showing a calculation result (3D-SIM) of the relationship between the relative energy distribution ΔU/U and the relative temporal distribution ΔT/T, in the case where ions traveled on a path dislocated from the central axis of a single-stage reflectron.

FIG. 5A shows a calculation result (3D-SIM) of the relationship between the discrepancy Rdet from the central axis of the ions which arrived at a detector and the relative energy distribution $\Delta U/U$, and FIG. 5B shows a calculation result (3D-SIM) of the relationship between the relative energy distribution $\Delta U/U$ and the relative temporal distribution $\Delta T/T$, in the case where the ions traveled on a path parallel to and dislocated from the central axis of the reflectron (with the amount of displacement denoted by R). Using the time of flight for R=0 mm and $\Delta U/U$=0 as the reference value, the discrepancy from the reference value was calculated as $\Delta T$. FIG. 5A demonstrates that no divergence occurs within the range of $\Delta U/U$<−0.2, since ions are reflected by the uniform electric field in the region before the first-order focusing position and cannot reach the correcting potential region. A divergence occurs within the range of $-0.2 \leq \Delta U/U \leq 0.2$ where ions are reflected in the correcting potential region. However, since the discrepancy from the uniform electric field is small, the equipotential surfaces are approximately parallel to each other and the divergence is suppressed to the minimum. The extent of divergence increases with the increase in the displacement R.

Figure 6:
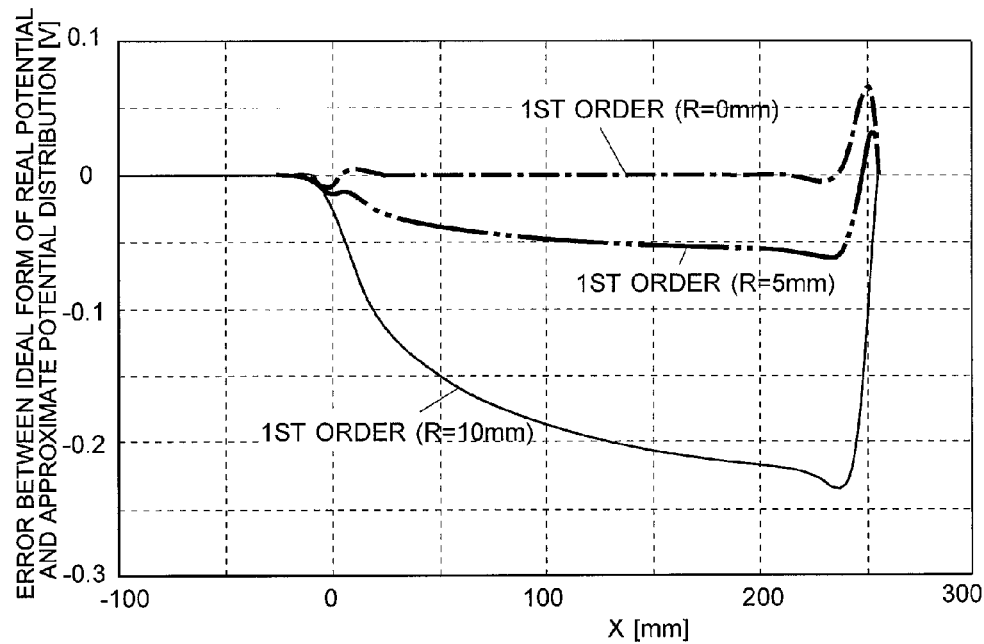
FIG. 6 is a graph showing an error between an ideal form of the real potential (1D-IDL) for a single-stage reflectron and a three-dimensional approximate potential distribution (3D-SIM) corresponding to that ideal form.

FIG. 6 shows an error between an ideal form of the real potential (1D-IDL) for a single-stage reflectron and a three-dimensional approximate potential distribution (3D-SIM) corresponding to that ideal form. As shown, a significant discrepancy has occurred at the starting point of the correcting potential even in the case of R=0 mm. This is due to the fact that, as already stated, the correcting potential $X_C(U)$ in the vicinity of the starting point of the correcting potential (X=0) is approximated by a half-integer power (2.5) and this functional form causes a divergence of the higher-order differential coefficients relating to the position. As a result, a considerably large magnitude of relative temporal distribution has occurred at the starting point of the correcting potential, as shown in FIG. 5B. This off-axis temporal aberration is approximately proportional to the square of the displacement R. Therefore, to suppress the off-axis temporal aberration, it is necessary to use a spatial area which lies close to the central axis and has a small displacement R. In the present case, the graph suggests that a mass-resolving power of 50,000 can be achieved within the range of $-0.2 \leq \Delta U/U \leq 0.2$ by limiting the displacement R to approximately 3 mm. Naturally, an even larger spatial distribution of the ions will be allowable if the mass-resolving power can be sacrificed. From the results described thus far, it has been confirmed that a practical isochronism can be achieved even by an approximate potential distribution created by a limited number of guard-ring electrodes.

Although the single-stage reflectron described thus far requires a somewhat long ion reflector and has a greater total length than the dual-stage reflectron (which will be described later), an advantage exists in that it requires a fewer number of grid electrodes and hence has a comparatively low probability of the ion loss due to the collision with the grid electrodes, so that the sensitivity can be more easily improved. However, since it merely satisfies the first-order focusing condition of $(dT/dE)_{E=1}=0$, the discrepancy from the uniform electric field, or the curvature of the potential distribution, will be larger than in the case where the second-order focusing condition, i.e. $(dT/dE)_{E=1}=0$ and $(d^2T/dE^2)_{E=1}=0$, is satisfied. The conventional, ideal reflectrons described in the documents of Cotter et al. or other references are designed without taking into account the focusing conditions higher than the first order. By contrast, in the present invention, the second-order focusing condition in the dual-stage reflectron is also newly taken into consideration, as will be hereinafter described.

[The Case of Dual-Stage Reflectron]

Figure 7:
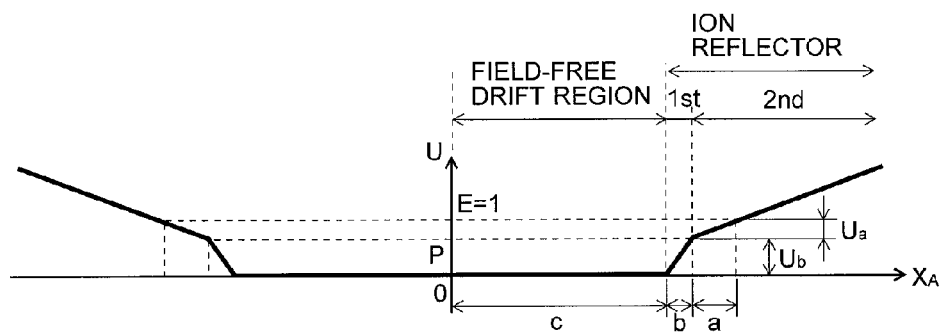
FIG. 7 is a schematic profile of a base potential to be used as a basis for determining an ideal form of the real potential for a dual-stage reflectron.
Figure 24:
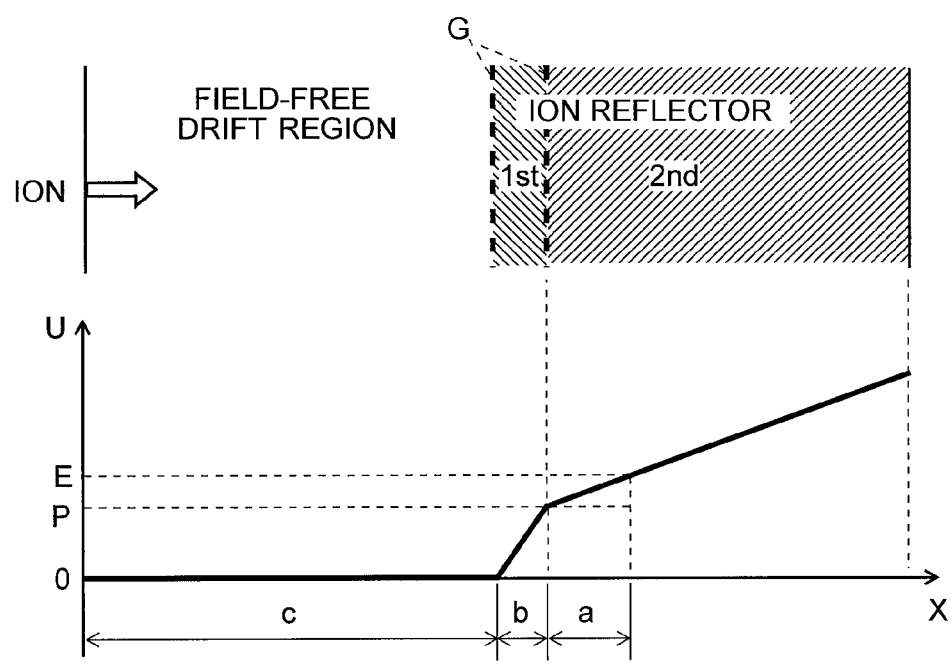
FIG. 24 is a schematic potential chart of a commonly used dual-stage reflectron.

Hereinafter described is an example in which the method of designing a TOFMS according to the present invention is applied to a dual-stage reflectron having two uniform electric fields. As in the case of the previously described single-stage reflectron, the base potential $X_A(U)$ has, as shown in FIG. 7, a laterally symmetrical shape with respect to X=0 (i.e. a shape obtained by expanding the potential profile shown in FIG. 24 into a laterally symmetrical form with respect to X=0). Specifically, the following equations (11) are considered as a potential distribution connecting two regions each of which has a uniform electric field:

$$X_A(U)=c+b(U/U_b) \text{ (for } 0 \leq U \leq U_b)$$

$$X_A(U)=c+b+a\{(U-U_b)/U_a\} \text{ (for } U_b \leq U) \quad (11)$$

Equations (11) are only valid for $X_A(U) \geq 0$; the potential for $X_A(U)<0$ can be obviously determined because of the lateral symmetry. Under such conditions, the time of flight $T_D(E)$ for one turn in the dual-stage reflectron is given by the following equation (12-1):

$$T_D(E)=4[c\sqrt{2E/m}+(b/U_b)[\sqrt{2mE}-\sqrt{2m(E-U_b)}]+(a/U_a)\sqrt{2m(E-U_b)}] \quad (12\text{-}1)$$

Using the mass m=1 and the energy $U_a+U_b=1$ as the reference values, as well as $U_b=p$, equation (12-1) can be simplified as follows:

$$T_D(E)=4(T_{free}(E)+T_{ref\text{-}a}(E)+T_{ref\text{-}b}(E)) \quad (12\text{-}2)$$

$$T_{free}(E)=c\sqrt{2E} \quad (12\text{-}3)$$

$$T_{ref\text{-}a}(E)=\{a/(1-p)\}\sqrt{2(E-p)} \quad (12\text{-}4)$$

$$T_{ref\text{-}b}(E)=(b/p)[\sqrt{2E}-\sqrt{2(E-p)}] \quad (12\text{-}5)$$

where, as in the case of the single-stage reflectron, $T_{free}(E)$ is the period of time for an ion to pass through the field-free drift region, $T_{ref\text{-}a}(E)$ is the period of time required for the ion to fly within the second stage consisting of a uniform electric field, and $T_{ref\text{-}b}(E)$ is the period of time required for the ion to pass through the first stage consisting of a uniform electric field. When the second-order focusing condition of $(dT_0/dE)_{E=1}=0$ and $(d^2T_0/dE^2)_{E=1}=0$ is imposed, the aforementioned condition of equations (2) will be obtained. Under the condition of $E \leq p$, since ions are reflected in the first stage, the time of flight T(E) for one turn over the entire range of energy will be expressed by the following equations (12-6):

$$T_D(E) = 4\{T_{free}(E) + (b/p)\sqrt{2E}\} \quad \text{(for } 0 \leq E \leq p)$$

$$T_D(E) = 4\{T_{free}(E) + T_{ref\text{-}a}(E) + T_{ref\text{-}b}(E)\} \quad \text{(for } p \leq E) \quad (12\text{-}6)$$

Figure 8:
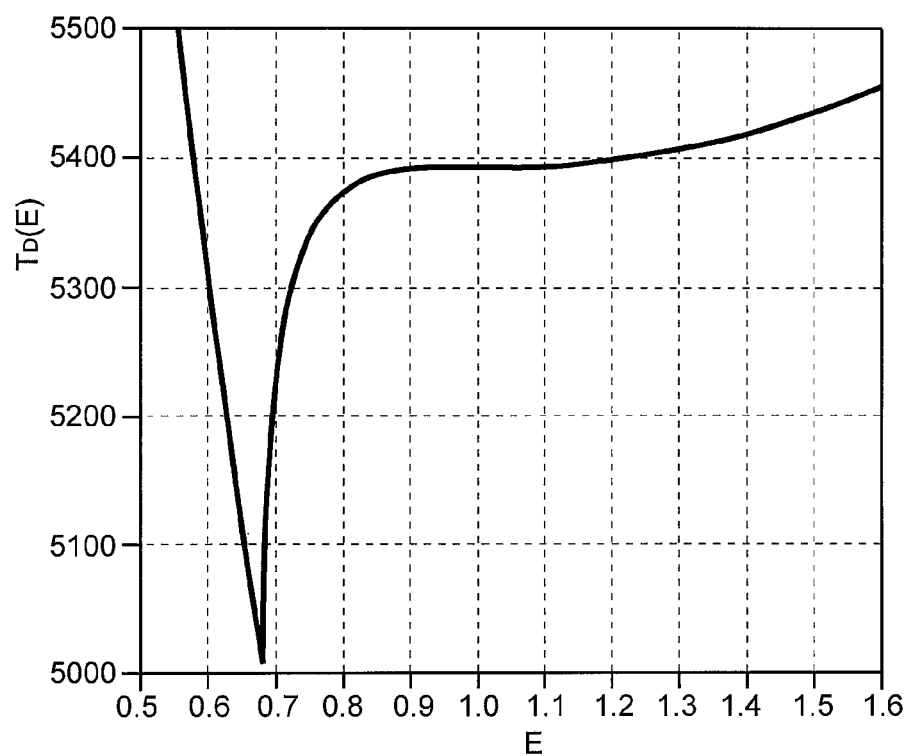
FIG. 8 is a graph showing a relationship between the energy E and the time of flight $T_D(E)$ for one turn when c=1,400 mm and b=30 mm in the system shown in FIG. 7.

As one example, FIG. 8 shows a calculation result of the relationship between the energy E and the time of flight $T_S(E)$ for one turn when c=1,400 mm and b=30 mm. In the graph shown in FIG. 8, the curve is not smoothly connected at E=p(=0.68). When the energy is E=1, the differential coefficients of up to the second order are zeroed, which confirms that the second-order focusing condition (the cancellation of the first and second-order terms in equation (5)) is satisfied. The solution thus obtained is none other than the conventional technique of Mamyrin solution.

At this point, the possibility of obtaining a real potential $X_R(U)$ which exactly achieves isochronism is explored by adding an extremely small correcting potential $X_C(U)$ to the base potential $X_A(U)$ created by the uniform electric field. Ideally, it is expected that a solution which satisfies the following conditions is the best solution: in FIG. 8, the time of flight $T_D(E)$ for one turn is $T_D(E) = T_S(1)$ (constant) for $E \geq 1$, $T_D(E)$ is smoothly connected at E=1, and a complete energy isochronism is achieved within the range of $E \geq 1$. In this situation, the correcting potential is to be superposed on the base potential $X_A(U)$ within the range of $\|X\| \geq (a+b+c)$, which in the best case scenario should make the real potential $X_R(U) = X_A(U) + X_C(U)$ smoothly connected at $X_R = a+b+c$. As in the case of the single-stage reflectron, equation (8) can be rewritten into the following relational expressions similar to equations (9), despite the difference in the time of flight T(E) for one turn:

$$X_R(U) = \frac{1}{2\pi\sqrt{2}} \int_0^U \frac{T(E)\,dE}{\sqrt{U-E}} \quad (13\text{-}1)$$

$$= \frac{1}{2\pi\sqrt{2}} \left[ \int_0^1 \frac{T_D(E)\,dE}{\sqrt{U-E}} + \int_0^U \frac{T_D(1)\,dE}{\sqrt{U-E}} \right]$$

$$= \frac{1}{2\pi\sqrt{2}} \left[ \int_0^U \frac{T_D(E)\,dE}{\sqrt{U-E}} + \int_1^U \frac{(T_D(1) - T_D(E))\,dE}{\sqrt{U-E}} \right]$$

$$= X_A(U) + X_C(U)$$

$$X_A(U) = \frac{1}{2\pi\sqrt{2}} \int_0^U \frac{T_D(E)}{\sqrt{U-E}}\,dE \quad (13\text{-}2)$$

$$X_C(U) = \frac{1}{2\pi\sqrt{2}} \int_1^U \frac{T_D(1) - T_D(E)}{\sqrt{U-E}}\,dE \quad (13\text{-}3)$$

In these expressions, the base potential $X_A(U)$ represents a potential obtained by extending the uniform electric field of the second stage in equation (11) into the range of U>1, and the correcting potential $X_C(U)$ represents the discrepancy from that uniform electric field.

Figure 9A:
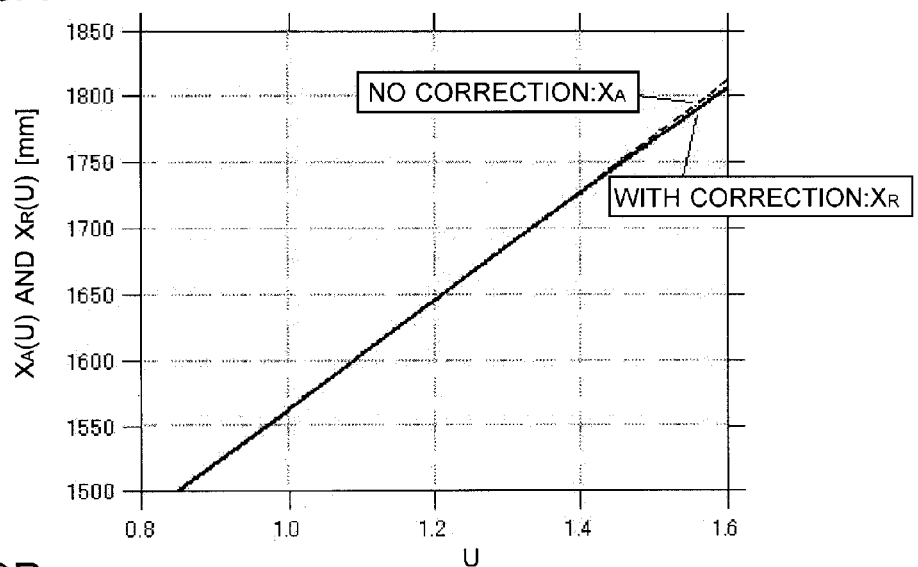
FIG. 9A is a graph showing a calculation result (1D-IDL) of the real potential $X_R(U)$ and the base potential $X_A(U)$ in the system shown in FIG. 7.

Due to the second-order focusing condition, $(dT_D/dE)_{E=1} = 0$ and $(d^2T_D/dE^2)_{E=1} = 0$, $T_D(1) - T_D(E)$ is reduced to an extremely small, third-order quantity for the energy difference (E−1), so that the correcting potential $X_C(U)$ becomes even smaller than in the case of the single-stage reflectron. This means that the dual-stage reflectron is more capable of suppressing the influence of the unwanted divergence of the ions. FIG. 9A shows a calculated result (1D-IDL) of the real potential $X_R(U)$. As in case of the single-stage reflectron, the potential for $U \leq 1$ is the base potential $X_A(U)$ created by a uniform electric field, while the potential for $U \geq 1$ is composed of the base potential $X_A(U)$ of the uniform electric field of the same strength with an extremely small correcting potential $X_C(U)$ added thereto. As can be seen in FIG. 9A, the real potential $X_R(U)$ is smoothly connected at U=1 (which corresponds to $X_R(1) = a+b+c = 1562.3$ mm), and the correcting potential $X_C(U)$ is much smaller than the base potential $X_A(U)$ created by the uniform electric field. Therefore, it is expected that the correcting potential $X_C(U)$ can be realized with a practical level of accuracy by applying an appropriate voltage to each of the grid-less guard-ring electrodes. Furthermore, due to the same reason, it is also expected that no significant divergence of ions will occur.

Figure 9B:
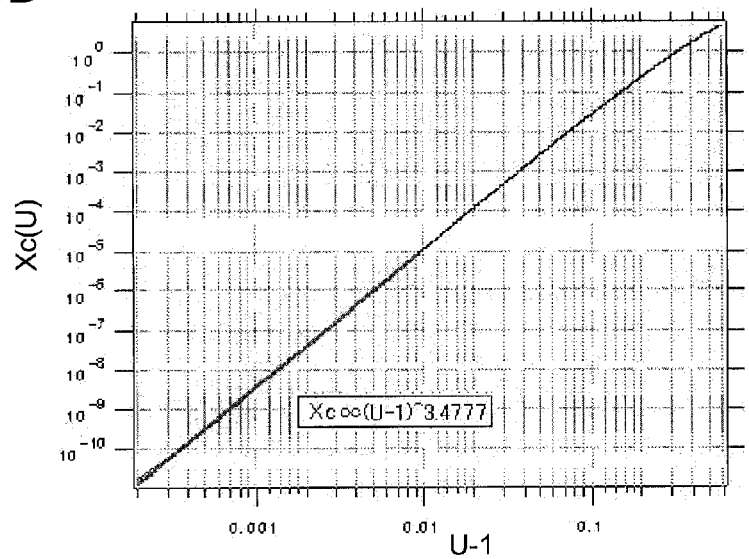
FIG. 9B is a graph showing a calculation result (1D-IDL) of the correcting potential $X_C(U)$.

FIG. 9B is a double logarithmic graph (1D-IDL) on which the correcting potential $X_C(U)$ is plotted, with the abscissa indicating U−1. In the present case, the correcting potential lies on an approximately straight line, maintaining the relationship of $X_C(U) \propto (U-1)^{3.5}$ within a range where U−1 is small. This result shows that the amount of correction is smaller than the Wiley-McLaren solution, $X_C(U) \propto (U-1)^{2.5}$.

FIG. 10A is a conceptual diagram showing a relationship between the base potential created by a uniform electric field and the real potential in a dual-stage reflectron. The correcting potential $X_C(U)$ is added within the section extending from the second-order focusing position into the deeper region as viewed from the side on which ions enter the ion reflector.

Using the base potential $X_A(U)$ and the real potential $X_R(U)$ obtained in the previously described manner, the relative value ($\delta T/T$) of the discrepancy of the time of flight with respect to the initial energy has been calculated for an ion which begins flying from the coordinate X=0 in the positive direction of the X axis and which is then reflected by the ion reflector and arrives at the detector placed at the coordinate X=0. The time of flight can be calculated by the following equation (14):

$$TOF(E) = 2 \int_0^{X_E} \frac{dX}{v} \quad (14)$$

$$= 2 \int_0^{X_E} \frac{dX}{\sqrt{2(E - U(X))}}$$

$$= 2 \left[ \int_0^c \frac{dX}{\sqrt{2E}} + \int_c^{b+c} \frac{dX}{\sqrt{2(E - U_1(X))}} + \int_{b+c}^{a+b+c} \frac{dX}{\sqrt{2(E - U_2(X))}} + \int_{a+b+c}^{X_E} \frac{dX}{\sqrt{2(E - U_3(X))}} \right]$$

where $X_E$ is the X coordinate of the turn-around point (position) of the ion, and $U_1(X)$, $U_2(X)$ and $U_3(X)$ are potential distributions within the ranges of $c \leq x \leq b+c$, $b+c \leq x \leq a+b+c$ and $X \geq a+b+c$, respectively.

Figure 11:
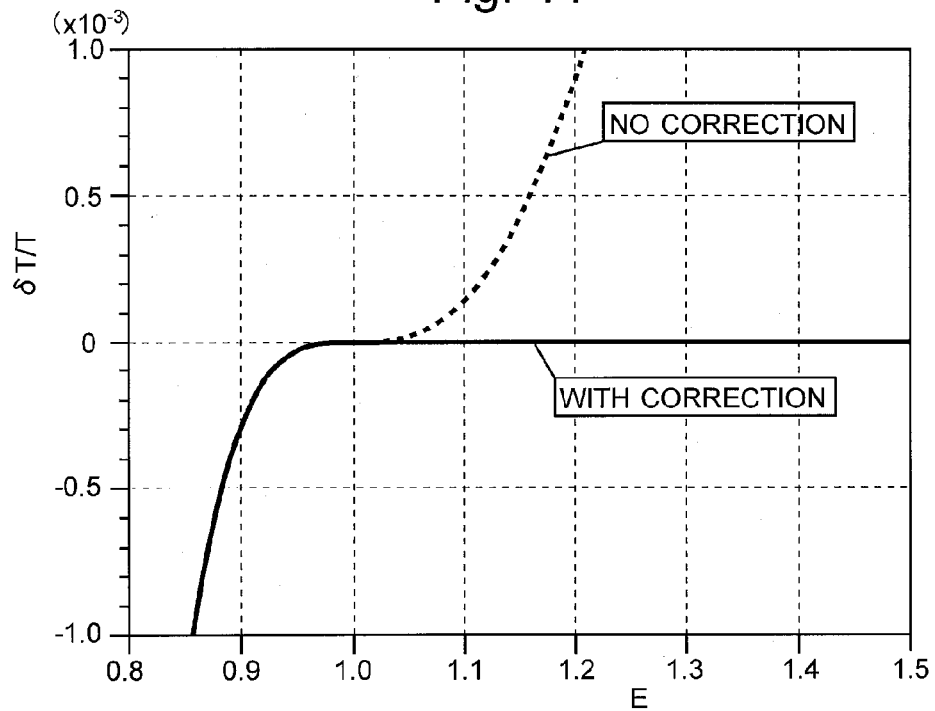
FIG. 11 is a graph showing a calculation result (1D-IDL) of the relationship between the relative value δT/T of the discrepancy of the time of flight and the initial energy in the system shown in FIG. 7.

FIG. 11 shows the result (1D-IDL) of the calculation of the relative value ($\delta T/T$) of the discrepancy of the time of flight with respect to the initial energy for the cases with or without the correcting potential $X_C(U)$. Without the correcting potential $X_C(U)$ (i.e. in the case of the conventional Mamyrin solution), the range within which the discrepancy of the time of flight is small is considerably narrow; the energy range where $\delta T/T \leq 10^{-4}$ (mass-resolving power, 5,000) is achieved is approximately ±8%, and the energy range where $\delta T/T \leq 10^{-5}$ (mass-resolving power, 50,000) is achieved is approximately ±4%. By contrast, in the case where the correcting potential $X_C(U)$ is added, an exact isochronism is achieved within the range of $E \geq 1$. Although calculation was limited to the range of $E \leq 1.5$, it has still been confirmed that $E = 1.25 \pm 0.25$, i.e. that a complete energy focusing can be achieved (on the central axis) over a broad energy range of ±20%. The energy focusing is exactly achieved even if E≥1.5. Therefore, the energy focusing of ions having an even broader energy distribution can be completely achieved by increasing the length of the ion reflector as needed.

The largest difference between the graphs with or without correction in FIG. 4 is whether or not the lower and higher energy sections of the curve are symmetrical with respect to the boundary line E=1. The result (1D-IDL) without correction is symmetrical with respect to the point E=1, whereas the symmetry is completely broken in the case of the graph with correction. Such a disappearance of symmetry cannot occur in a multi-stage reflectron; to realize such a state, it is necessary to add a correcting potential $X_C(U)$ which is satisfies $X_C(U) \propto (U-1)^{3.5}$ and cannot be extended into the lower-energy region (U<1). In other words, a half-integer power, or more specifically, the $3.5^{th}$ power, is indispensible for creating such an asymmetrical state.

The dual-stage reflectron described thus far requires two grid electrodes and hence causes a greater amount of ion loss due to the collision with the grid electrodes as compared to the single-stage reflectron. However, an advantage exists in that the ion reflector can be shortened and the total length of the system will be reduced. More importantly, the influence of the problem of the unwanted divergence of the ions will be more suppressed since the amount of correcting potential is small.

As described thus far, it is theoretically certain that an ideal potential distribution can be obtained by the design method of a reflectron adopted in the present invention. However, a divergence of the high-order differential coefficients relating to the position of the ideal form of the real potential $X_A(U)$ inevitably occurs because, as stated earlier, the correcting potential $X_C(U)$ in the vicinity of the starting point of the correcting potential is approximated by a half-integer power (3.5). Therefore, it is necessary to confirm that such a real potential can be created by a practical hardware system. Accordingly, the present inventors have conducted a simulation (3D-SIM) for determining whether the aforementioned real potential can be created by a realistic number of guard-ring electrodes. In the hereinafter described example, the dual-stage reflectron has the dimensions of c=1,400 mm and b=30 mm, with the second stage measuring 370 mm in length. The guard-ring electrodes have 80 electrodes arranged at intervals of 5 mm, with each electrode measuring 40 mm in inner diameter and 0.2 mm in thickness. In this system, the potential is corrected within the range of equal to or higher than 5600 V so as to enable the energy focusing of the ions with an energy distribution of 7 keV±20%. An appropriate voltage was applied to each of the guard-ring electrodes so as to create an ideal potential on the central axis of the reflectron.

Figure 12:
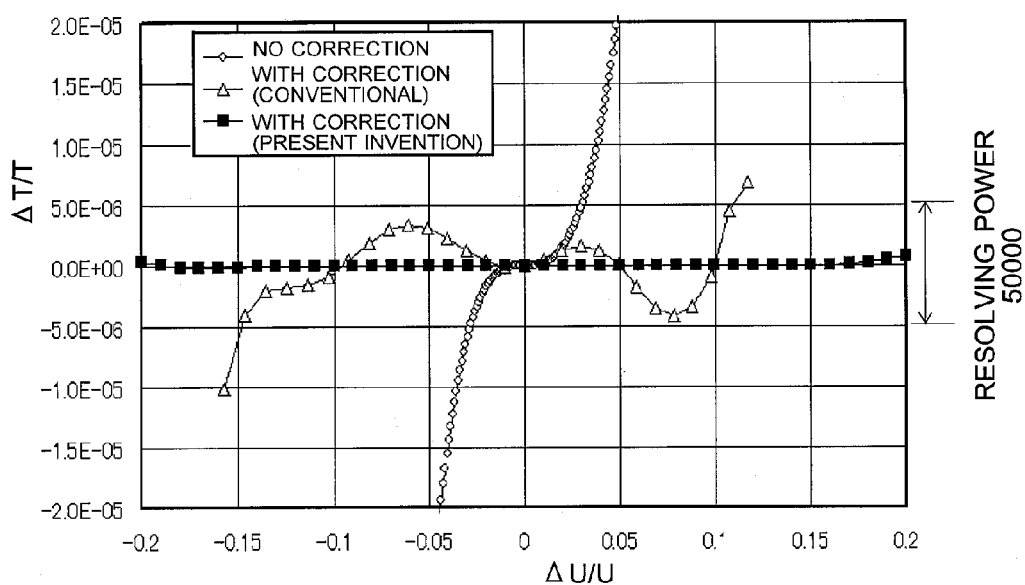
FIG. 12 is a graph showing a calculation result (3D-SIM) of the relationship between the relative energy distribution ΔU/U and the relative temporal distribution ΔT/T in the case where ions travel on the central axis of an ion reflector.

FIG. 12 shows the simulation result (3D-SIM) of the relative temporal distribution ΔT/T with respect to the relative energy dispersion ΔU/U in the case where ions traveled on the central axis of an ion reflector. Also shown in the figure is the level of the Mamyrin solution with no correcting potential (a reproduction of the state of "no correction" in FIG. 11) as well as a simulation result obtained by using Patent Document 3 as a level of the existing techniques. When the conventional technique according to Patent Document 3 is used, higher levels of resolving power can be achieved over a broader energy distribution than in the case of the state of "no correction." However, when the energy distribution exceeds the range of 10-15%, the temporal distribution becomes considerably large and the mass-resolving power deteriorates. By contrast, as a result of the correction based on the technique according to the present invention, a high level of isochronism on the order of $10^{-6}$ in terms of the relative temporal distribution ΔT/T is achieved (on the central axis) even if the energy distribution is as large as ±20%. Thus, it has been confirmed that the aforementioned technique is effective even in the case of using a limited number of guard-ring electrodes.

Figure 13A:
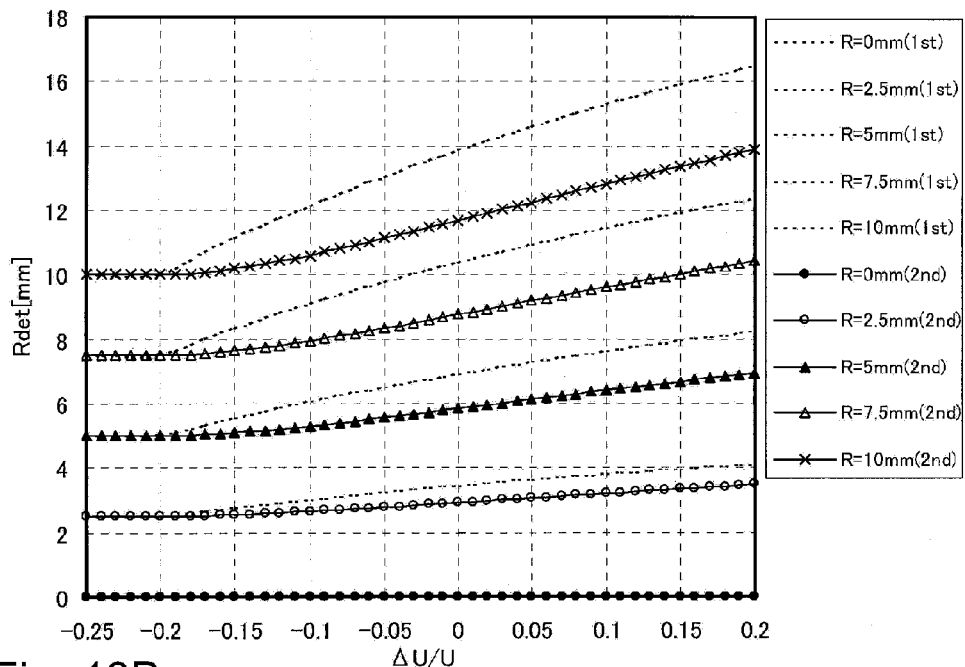
FIGS. 13A and 13B are graphs showing calculation results (3D-SIM) of the displacement Rdet from the central axis of the ions which arrived at a detector and the relative temporal distribution ΔT/T, with respect to the relative energy distribution ΔU/U, in the case where ions travel on a path dislocated from the central axis of a dual-stage reflectron.
Figure 13B:
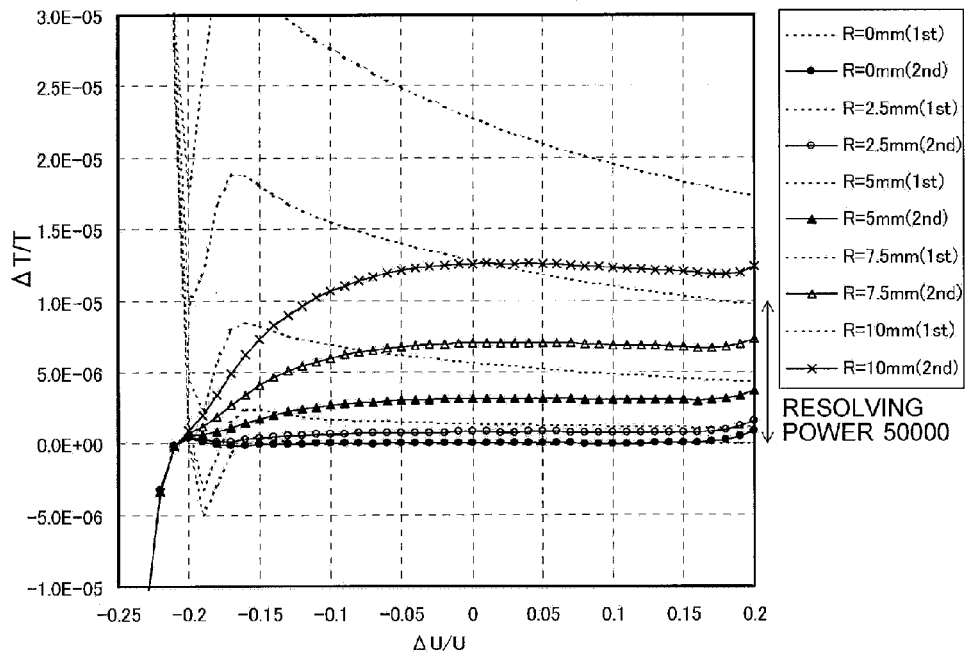

Another simulation has been conducted to investigate the temporal aberration due to the off-axis location, i.e. to investigate to what degree the mass-resolving power deteriorates in the case where ions travel on a path dislocated from the central axis of the reflectron. FIGS. 13A and 13B show simulation results (3D-SIM) of the discrepancy Rdet from the central axis of the ions which arrived at a detector and the relative temporal distribution ΔT/T, with respect to the relative energy distribution ΔU/U, in the case where ions travel on a path dislocated from the central axis of the dual-stage reflectron (with the amount of displacement denoted by R). Using time of flight for R=0 mm and ΔU/U=0 as the reference value, the discrepancy from this reference value was calculated as ΔT. For comparison, the result (3D-SIM) obtained for a single-stage reflectron is also shown by the dashed lines.

According to FIG. 13A, no divergence occurs within the range of ΔU/U<-0.2, since ions are reflected by the uniform electric field in the region before the second-order focusing position and cannot reach the correcting potential region. A divergence occurs within the range of -0.2≤ΔU/U≤0.2 where ions are reflected in the correcting potential region. However, since the discrepancy from the uniform electric field is small, the equipotential surfaces are approximately parallel to each other and the divergence is suppressed to the minimum. The extent of divergence increases with the increase in the displacement R. The extent of divergence in the case of the dual-stage reflectron is smaller than in the case of the single-stage reflectron.

Figure 14:
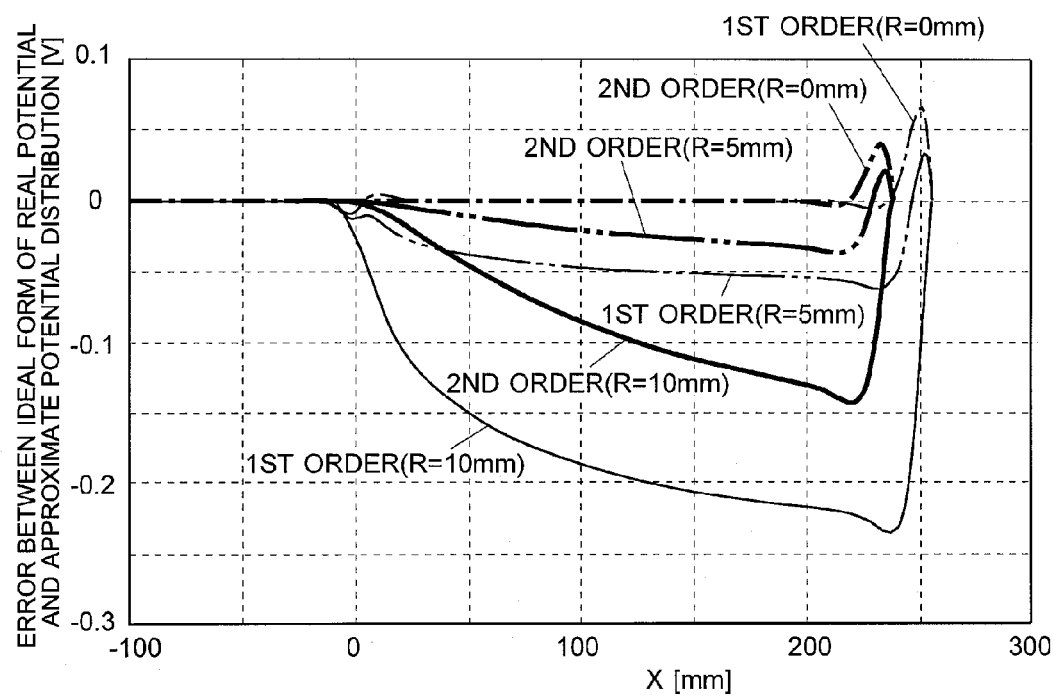
FIG. 14 is a graph showing an error between an ideal form of the real potential (1D-IDL) for a dual-stage reflectron and a three-dimensional approximate potential distribution (3D-SIM) corresponding to that ideal form.

FIG. 14 shows an error between an ideal form of the real potential (1D-IDL) for a dual-stage reflectron and a three-dimensional approximate potential distribution (3D-SIM) corresponding to that ideal form. The graph shows that a considerable discrepancy from the curve of R=0 mm occurs at the starting point of the correcting potential, which is because the correcting potential $X_C(U)$ in the vicinity of the starting point of the correcting potential is approximated by the power of a half integer (3.5) and hence the higher-order differential coefficients relating to the position of the ideal form of the real potential $X_R(U)$ diverge. However, as compared to the single-stage reflectron, the dual-stage reflectron has a smaller discrepancy at the starting point of the correcting potential.

In FIG. 13B, there is no dependency of the time of flight on the displacement R within the range of ΔU/U<-0.2, since the ions within this range are reflected by the uniform electric field in the region before the second-order focusing position and cannot reach the correcting potential region. On the other hand, within the range of -0.2≤ΔU/U≤0.2, where the ions are reflected by the correcting potential region, the mass-resolving power deteriorates as a result of the temporal aberration due to the off-axis location as the displacement of the ion path from the central axis becomes larger. This off-axis aberration is approximately proportional to the square of the displacement R. Therefore, it can be said that, to suppress the off-axis temporal aberration, it is necessary to use a spatial area which lies close to the central axis and has a small displacement R. Nevertheless, the influence of the off-axis aberration is smaller than in the case of the single-stage reflectron; according to the simulation, the upper limit of the mass-resolving power (approximately 40,000 to 50,000) of the currently available TOFMS systems can be achieved by merely limiting the ion path within a range of R≤10 mm from the central axis. A comparison of the result (3D-SIM) of the dual-stage reflectron with the result (3D-SIM) of the single-stage reflectron demonstrates that the dual-stage reflectron has a smaller divergence in the reflector and a smaller off-axis aberration. Accordingly, it can be said that using the second-order focusing condition is more preferable. From these results (3D-SIM), it has been confirmed that a practical isochronism can be achieved even by an approximate potential distribution created by a limited number of guard-ring electrodes.

A supplementary explanation on the off-axis aberration is hereinafter given. A primary cause of the off-axis aberration is the error of the actual potential distribution from the ideal potential distribution. The potential distribution U(R, X) inside the reflector is given by the following equation (15):

$$U(R,X) = \Phi(X) - A \cdot R^2 \Phi''(X) \tag{15}$$

where $\Phi(X)$ is the potential on the central axis, A is a constant determined by the opening shape of the guard-ring electrodes, and $\Phi''(X)$ is the second derivative of $\Phi(X)$. Equation (15) shows that there are two possible methods for reducing the influence of the off-axis aberration: decreasing the displacement R or making the second derivative $\Phi''(X)$ of the potential smaller. Accordingly, it can be said that a real potential $X_R(U)$ which satisfies the complete isochronism will be a practically more preferable solution if it is closer to a uniform electric field, because such a solution has a smaller value of the second derivative $\Phi''(X)$. That is to say, in a multi-stage reflectron, choosing the N-th order focusing position as the starting point of the correcting potential and increasing the order N makes the potential closer to a uniform electric field and hence is preferable for reducing the off-axis aberration.

To further decrease the influence of the off-axis aberration, a component for limiting the passing area of the ions, such as an aperture or slit, may be placed before the reflector so as to remove ions with large displacements R from the central axis. However, this method is disadvantageous in terms of sensitivity, because the amount of ions decreases. To avoid such a decrease in the amount of ions, it is preferable to insert a focusing lens (convex lens) between the ion source and the reflector, or to provide the ion source with the effect of the focusing lens, so as to reduce the spatial distribution of the ions entering the reflector and thereby decrease their displacement R.

In the previously described computer simulation, it was assumed that the opening of the guard-ring electrodes was shaped like a circular hole. The opening shape is not limited to this one; it is also possible to use guard-ring electrodes whose opening is shaped like a slit or elongated hole. In the case of a system in which ions are obliquely injected to the central axis of the reflectron so as to allow spatial separation of the ion ejector and the detector, using the guard-ring electrodes with the opening shaped like a slit or elongated hole is convenient, because the spatial area in which a high mass-resolving power can be achieved can be widely ensured in one direction. Even in this case, excellent performances can be similarly achieved as in the case of the guard-ring electrodes whose opening is shaped like a circular hole.

[Examination of Correcting Potential Function]

The reason for the presence of a half-integer power (e.g. the $2.5^{th}$ or $3.5^{th}$ power) in the correcting potential function $X_C(U)$ in the previously described embodiments is hereinafter described. The basis of the following discussion is the principle of superposition which holds true between the real potential $X_R(U)$ and the time of flight T(E) for one turn.

What is implied by the aforementioned equation (8) is that the functions $X_R(U)$ and T(E) are combined together by a linear integral conversion, and therefore, the principle of superposition can be applied to the solution. That is to say, if $T_1(E)$ and $T_2(E)$ denote the times of flight for one turn for $X_{R1}(U)$ and $X_{R2}(U)$, respectively, the time of flight for one turn for the potential distribution $X_{R1}(U)+X_{R2}(U)$ will be $T_1(E)+T_2(E)$. The principle of superposition also naturally holds true in the case where the positions of the real potential $X_R(U)$ and the time of flight T(E) for one turn are transposed.

In the previous embodiments, only a single-stage reflectron and a dual-stage reflectron were described. The basic procedure of the present invention can be generalized as follows: First, with a system configuration of a single-stage or multi-stage reflectron as a reference model which approximately achieves isochronism, a base potential $X_A(U)$ is created inside the ion reflector, and an N-th order focusing position is created. Then, in the space extending from the N-th order focusing position into deeper regions, a non-uniform correcting potential $X_C(U)$ is superposed on the base potential $X_A(U)$ to obtain a real potential $X_R(U)$ as the final result. Therefore, in the case of the previously described single-stage reflectron, when no correcting potential $X_C(U)$ is present, the first-order differential coefficient is zero. Accordingly, when expanded into a Taylor series at around E=1, the time of flight for one turn is $T(E) \sim T(1) + a(E-1)^2$, and the second-order term $a(E-1)^2$ of the time of flight for one turn T(E) is cancelled by superposing the correcting potential $X_C(U)$ on the base potential $X_A(U)$ within the range of E≥1. Using equation (8), the correcting potential will be expressed as the following equation (16):

$$X_C(U) = \frac{1}{2\pi\sqrt{2}} \int_1^U \frac{a(E-1)^2}{\sqrt{U-E}} dE \propto (U-1)^{5/2} \tag{16}$$

This equation explains the result (1D-IDL) of FIG. 3B in which the discrepancy $X_C(U)$ from the base potential created by a uniform potential is approximately proportional to $(U-1)^{2.5}$.

Similarly, in the case of the dual-stage reflectron, when no correcting potential $X_C(U)$ is present, the first and second order differential coefficients are zero. When expanded into a Taylor series at around E=1, the time of flight for one turn is $T(E) \sim T(1) + b(E-1)^3$, and the third-order term $b(E-1)^3$ of the time of flight for one turn is cancelled by superposing the correcting potential $X_C(U)$ on the base potential $X_A(U)$ within the range of E≥1. This correcting potential is given by the following equation (17):

$$X_C(U) = \frac{1}{2\pi\sqrt{2}} \int_1^U \frac{b(E-1)^3}{\sqrt{U-E}} dE \propto (U-1)^{7/2} \tag{17}$$

This equation explains the result (1D-IDL) of FIG. 9B in which the discrepancy $X_C(U)$ from the base potential created by a uniform potential is approximately proportional to $(U-1)^{3.5}$.

To put it generally, when $(d^n T/dE^n)(E-E_0)^n$ in equation (5) is to be cancelled, the half-integer power $(U-E_0)^{n+1/2}$ is required in the correcting potential $X_C(U)$. That is to say, by using the following equation (18) obtained by expanding the correcting potential $X_C(U)$ into a half-integer power series, it is possible to correct the time of flight T(E) for one turn up to the n-th order in terms of energy (to zero the differential coefficients up to the n-th order), whereby a high level of isochronism can be achieved for ions whose energy E satisfies E≥1:

$$X_C(U) = \Sigma a_k (U-1)^{k+1/2} \tag{18}$$

where $\Sigma$ is the sum from k=1 to n.

According to the study by the present inventors, it is evident that, if the order number of the power in the correcting potential is not exactly a half integer (e.g. 2.5 or 3.5 in the previously described examples), the corresponding term (e.g. the second or third term) in equation (5) cannot be completely cancelled and the mass-resolving power will deteriorate. A quantitative estimation of the influence of the discrepancy of the order number of the power has revealed that, in the case of a dual-stage reflectron, an exponential value having a discrepancy of about 0.1 from 3.5 prevents the system from maintaining a mass-resolving power of approximately 10,000 with an energy width of 10%. However, the influence of the discrepancy of the exponential value will be lessened as the number of stages of the ion reflector increases. Furthermore, the tolerance for the discrepancy of the exponential value will be greater if the ions to be focused have a narrower energy distribution. Based on these results, the "half-integer power" or "N+½" in the present invention can be interpreted as a range of exponential values with an allowance of approximately 0.2, i.e. the double of 0.1, which may be expressed as an exponential value of "N+1.5±0.2" or an exponential-value range of "N+1.3 to N+1.7."

The range in which the distribution of the correcting potential $X_C(U)$ can be satisfactorily expressed by a half-integer power is limited to the vicinity of the boundary at which the correcting potential begins. According to the previously described embodiments (see FIGS. 3B and 9B), the correcting potential $X_C(U)$ can be satisfactorily represented by a half-integer power within the range of $0 \leq U-1 \leq 0.01$. Increasing this range causes the exponential value to have a greater discrepancy from the half-integer value. For example, in the case of the dual-stage reflectron, the exponential value is 3.48 within the range of $0 \leq U-1 \leq 0.01$, while the value becomes 3.30 if the range is widened to $0 \leq U-1 \leq 0.1$. Based on this result, and taking into account the aforementioned allowable range of the exponential value being approximately 0.2, the "region in the vicinity of the boundary of the starting point" in the present specification is a spatial range which satisfies the condition of approximately $0 \leq U-1 \leq 0.1$.

The range of the "N-th order focusing position" is hereinafter described. A single-stage or multi-stage ion reflector with the base potential created by only a uniform electric field or fields before the superposition of the correcting potential $X_C(U)$ for achieving isochronism is considered as a reference model. With RSa denoting a practical target level of the mass-resolving power, the ion-reflecting space area inside the reflector in which the mass-resolving power RSa can be achieved by using the N-th order focusing condition is denoted by S, and this ion-reflecting space area S is defined as the range of the "N-th order focusing position" which corresponds to the starting point of the superposition of the correcting potential. A specific example is hereinafter described, in which the second-order focusing condition is used in a dual-stage reflectron.

Figure 15A:
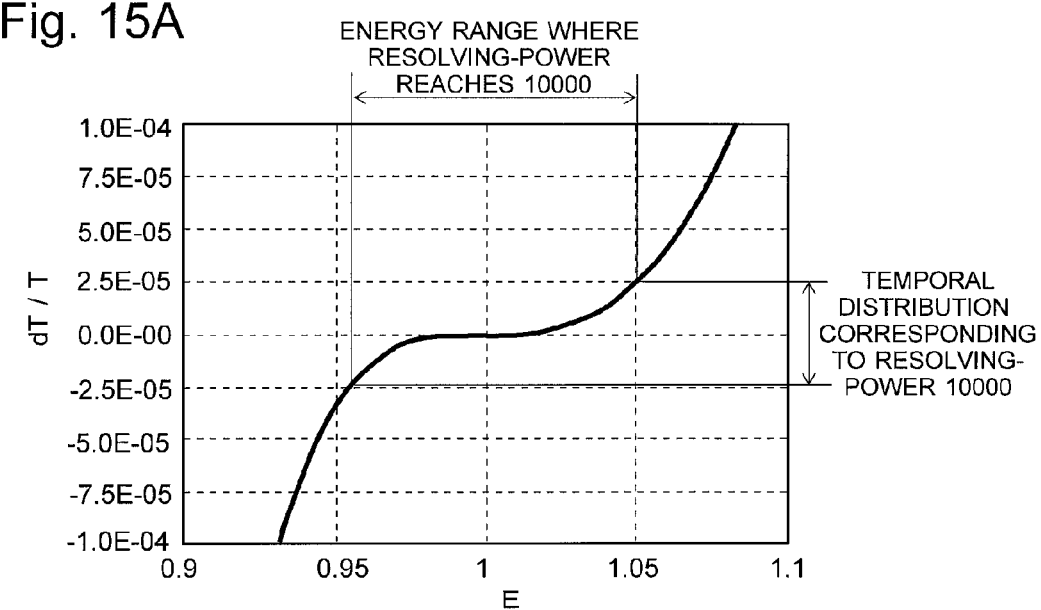
FIG. 15A is a graph showing a relationship between the initial energy E and the relative temporal distribution dT/T in a dual-stage reflectron composed of only uniform electric fields.

When no correcting potential is superposed (i.e. in the case of the conventional Mamyrin solution), the relationship of the relative temporal distribution dT/T with respect to the initial energy E will be as shown in FIG. 15A, where the field-free drift length is c=1,000 mm and the first-stage length is b=100 mm. If the target mass-resolving power is RSa=10,000, since RSa=T/(2ΔT), the temporal distribution dT/T corresponding to the target mass-resolving power is $5 \times 10^{-5}$. As can be seen in FIG. 15A, the energy range corresponding to the target mass-resolving power is E≈0.955-1.05.

Figure 15B:
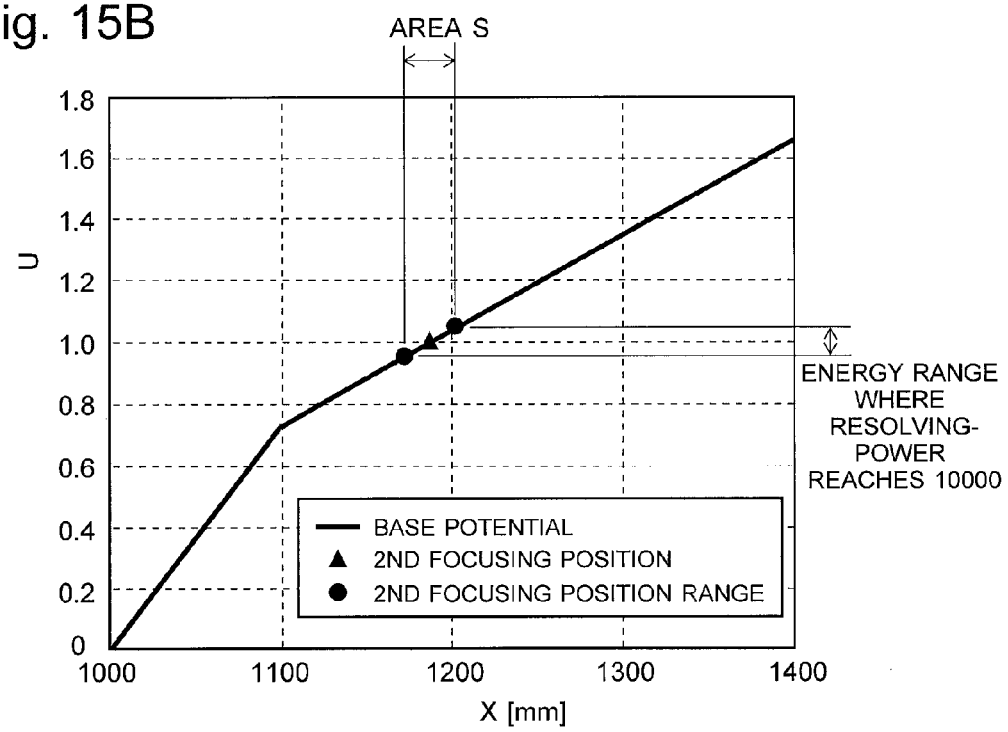
FIG. 15B is a graph showing the base potential inside the reflector.

FIG. 15B is a graph showing the base potential inside this reflector. An incident ion of energy E=1 is reflected at the second-order focusing position (X=1186.4 mm), and the second-order focusing is achieved from FIG. 15A. This area S (X≈1171.9-1202.6 mm) in which the ions included in the energy range corresponding to the target mass-resolving power (E≈0.955-1.05) is regarded as the spatial range of the "second-order focusing position" in the present specification. If the starting point of the correcting potential is outside this spatial area, the error of the potential distribution in the vicinity of the starting point of the correcting potential (the N-th order focusing position) considerably increases, causing a significant temporal aberration. Therefore, it is difficult to achieve the target mass-resolving power.

[Verification of Applicability to Non-Periodic Motion]

The case of handling a non-periodic motion by the previously described method of achieving isochronism by the superposition of the correcting potential on the base potential is subsequently described.

Since the aforementioned equation (8) is a clear integral equation, it was possible to deduce a new finding for an ideal reflectron and to conceive the previously described technique based on that finding. However, a problem exists in that equation (8) is only applicable to periodic motions; it is totally impossible to handle non-periodic motions. On the other hand, in actual TOFMSs, there are components which cause deviation from periodic motions; for example, the ion ejector (e.g. the ion source) is provided only on the forward path of the flying route of the ions; there is also a difference between the forward and return paths as to whether or not an ion-beam optical element, such as an ion lens or deflector, is present. Although the theory described in the documents of Cotter et al. is formulated so that it can also handle non-periodic motions, it is not evident whether or not the present inventors' finding, namely, that the superposition of the correcting potential on the base potential beginning from the N-th order focusing position is appropriate, is also applicable to non-periodic motions. Accordingly, a rigorous verification is hereinafter given for the case where the base potential is a uniform electric field.

Figure 16:
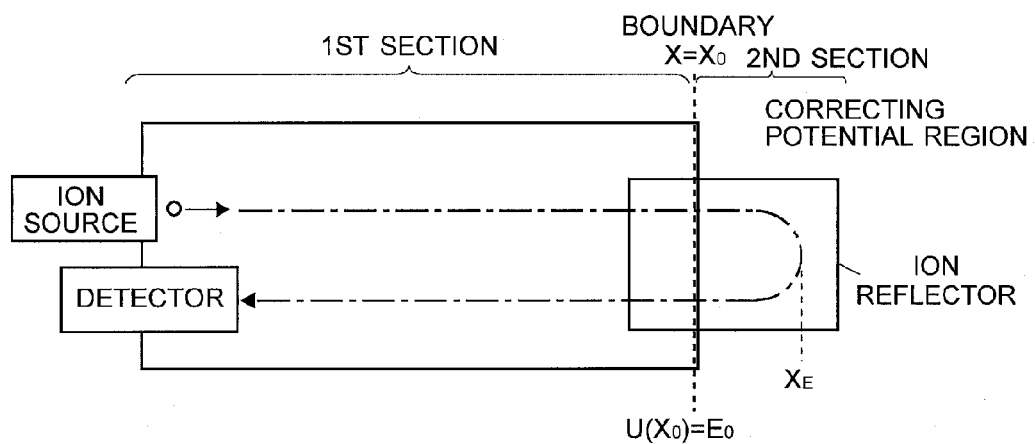
FIG. 16 is a modeled configuration diagram for analyzing the conditions for complete isochronism for a non-periodic motion.

Hereinafter, a system shown in FIG. 16 is considered as a modeled configuration of the TOFMS. This system has two sections, with the coordinate value $X=X_0$ and the potential value $U(X_0)=E_0$ as the boundary. The first section includes an area in which the aforementioned non-periodic elements are present, and a base potential composed of a uniform electric field created by a normal multi-stage ion reflector is present in the vicinity of the boundary. The second section includes a correcting potential region having a certain correcting potential superposed on the uniform electric field, whereby the total time of flight from the ion source to the detector is maintained at a constant value. Unlike the first section, the second section guarantees the complete symmetry between the forward and return paths.

Let T(E) denote the total time of flight, $T_{A-1}(E)$ denote the sum of the times of flight on the forward and return paths in the first section, and $T_B(E)$ denote the sum of the times of flight on the forward and return paths in the second section. Then, the following equation (19-1) naturally holds true:

$$T(E) = T_{A-1}(E) + T_B(E) \qquad (19\text{-}1)$$

It should be noted that only the energy levels of $E \geq E_0$ are considered, and hence $T_B(E) \geq 0$. With $X_E$ denoting the turn-around point at energy E, the relationship between the time of flight in the second section and the potential distribution $U_B(E)$ in the correcting potential region is given by the following equation (19-2):

$$T_B(E) = 2 \int_{X_0}^{X_E} \frac{dX}{\sqrt{2(E - U_B(X))}} \quad (19\text{-}2)$$

It should be noted that the parameters q and m are normalized as q=m=1.

By multiplying both sides of equation (19-2) by $1/\sqrt{\alpha-E}$ and integrating it with respect to energy E from $E_0$ to $\alpha$, the potential distribution $\Delta X_B(\alpha)$ in the correcting potential region can be obtained, as expressed by the following equation (19-3):

$$\int_{E_0}^{\alpha} \frac{T_B(E)}{\sqrt{\alpha - E}} dE = \sqrt{2}\,\pi\{X_B(\alpha) - X_0\} = \sqrt{2}\,\pi \cdot \Delta X_B(\alpha) \quad (19\text{-}3)$$

Similarly, on the assumption that the base potential created by the uniform electric field in the vicinity of the boundary is extended into the correcting potential region instead of using $U_B(X)$ as the potential distribution in the correcting potential region, and that the period of time that ions spend in the correcting potential region is represented by $T_{A\text{-}2}(E)$ instead of $T_B(E)$, the following equation (19-4) can be obtained by substituting the variables into equation (19-3):

$$\int_{E_0}^{\alpha} \frac{T_{A-2}(E)}{\sqrt{\alpha - E}} dE = \sqrt{2}\,\pi \cdot \Delta X_A(\alpha) \quad (19\text{-}4)$$

where $\Delta X_A(\alpha)$ is the potential distribution created by extending into the correcting potential region the base potential created by the uniform electric field in the vicinity of the boundary.

By calculating the difference between equations (19-3) and (19-4), an indication of the amount of discrepancy between the potential distribution in the correcting potential region and the uniform electric field, i.e. $\Delta X_B(\alpha) - \Delta X_A(\alpha)$, can be calculated as shown in the following equation (19-5):

$$\sqrt{2}\,\pi \cdot (\Delta X_B(\alpha) - \Delta X_A(\alpha)) = \int_{E_0}^{\alpha} \frac{T_B(E) - T_{A-2}(E)}{\sqrt{\alpha - E}} dE \quad (19\text{-}5)$$
$$= \int_{E_0}^{\alpha} \frac{T(E) - T_{A-1}(E) - T_{A-2}(E)}{\sqrt{\alpha - E}} dE$$

It should be noted that equation (19-1) has been used to obtain the last equation.

In $E \geq E_0$, if the condition of complete isochronism (i.e. the total time of flight $T(E)=T(E_0)$=constant) is achieved, the following equation (19-6) is obtained:

$$\sqrt{2}\,\pi \cdot (\Delta X_B(\alpha) - \Delta X_A(\alpha)) = \int_{E_0}^{\alpha} \frac{T(E_0) - T_{A-1}(E) - T_{A-2}(E)}{\sqrt{\alpha - E}} dE \quad (19\text{-}6)$$
$$= \int_{E_0}^{\alpha} \frac{T(E_0) - T_A(E)}{\sqrt{\alpha - E}} dE$$

where $T_A(E)=T_{A\text{-}1}(E)+T_{A\text{-}2}(E)$. This $T_A(E)$ is the total time of flight which would be obtained if the base potential created by the uniform electric field was continuously extended from the first section into the second section. From equation (19-6), it can be easily understood that the smaller the value of $T(E_0) - T_A(E)$ in the integral equation is, the smaller the discrepancy $\Delta X_B(\alpha) - \Delta X_A(\alpha)$ from the uniform electric field is.

With $T(E_0)=T_A(E_0)$ taken into account, a Taylor expansion can be introduced into the equation, to obtain the following equation (19-7):

$$T(E_0) - T_A(E) = -(dT_A/dE)(E-E_0) - (\tfrac{1}{2})(d^2T_A/dE^2)(E-E_0)^2 - (\tfrac{1}{6})(d^3T_A/dE^3)(E-E_0)^3 - \ldots \quad (19\text{-}7)$$

From this equation, it is possible to rigorously verify that, even for a non-periodic motion, the N-th order focusing position is the best starting point for reducing the discrepancy of the potential from the uniform electric field.

In summary, for a system using a uniform electric field as the base potential, it has been verified that, even if important components that do not produce periodic motions (e.g. an ion source) are included, complete isochronism for the entire system including such components can be achieved by calculating the N-th order focusing position inside the ion reflector and superposing a correcting potential composed of an appropriate non-uniform electric field on the region deeper than the N-th order focusing position. This technique contrasts with the widely used conventional technique described in Non-Patent Document 3, in which ions ejected from an ion source are temporally focused and the focusing position is regarded as a virtual ion source of the reflectron. This is because, by this conventional technique, although complete isochronism can be achieved for the field-free drift region and the ion reflector, the aberration of the time focusing in the ion source inevitably remains until the end, thus preventing the system from achieving a high level of mass-resolving power.

In the previous description, it was assumed that a grid electrode was provided at the boundary of each stage of the multi-stage reflectron. It is also possible to assume an ion reflector having a grid-less structure and to design an ideal reflectron without grid electrodes by determining its internal potential distribution and the N-th order focusing position by numerical calculations, as in the case of the reflectron with grid electrodes. The configuration without grid electrodes has the merit that it is free from the ion loss due to the collision with the grid electrodes and hence advantageous for achieving high sensitivity.

As one embodiment of the non periodic motion described thus far, a system close to reality is hereinafter considered. Specifically, an orthogonal acceleration reflectron having a single-stage accelerating region created by a uniform electric field is considered as the ion source. The guard-ring electrodes are shaped like a slit (measuring 40 mm in width and 0.4 mm in thickness). The total length of the reflector is L=400 mm, with 40 electrodes arranged at intervals of 10 mm for ease of production. The length of the ion-accelerating region is d=4 mm, the field-free drift length is c=1,000 mm, and the first-stage length of the reflector is b=100 mm. A model diagram of the electrode shape and the potential profile used in the simulation (3D-SIM) is shown in FIG. 17.

Figure 17:
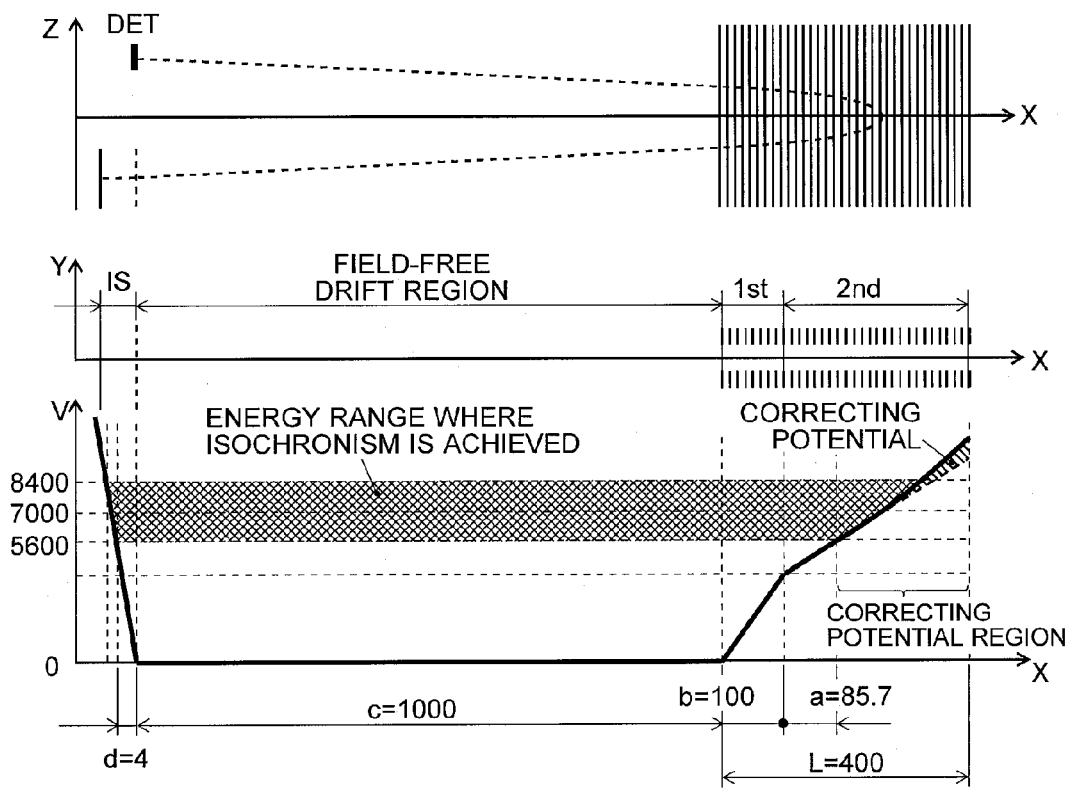
FIG. 17 is a model diagram showing the electrode shape and the potential shape used in a simulation performed for an orthogonal acceleration reflectron having a single accelerating region consisting of a uniform electric field.

In the case of the system shown in FIG. 17, which includes the ion-accelerating region and which has the base potential created by a uniform electric field, a simplified time of flight is given by the following equations:

$$T_{1D}(E) = T_{is}(E) + T_{free}(E) + T_{ref\text{-}a}(E) + T_{ref\text{-}b}(E)$$

$$T_{is}(E) = d/\sqrt{2E}$$

$$T_{free}(E) = 2c/\sqrt{2E}$$

$$T_{ref\text{-}a}(E) = \{2a/(1-p)\}\sqrt{2(E-p)}$$

$$T_{ref\text{-}b}(E) = (2b/p)[\sqrt{2E} - \sqrt{2(E-p)}]$$

where $T_{is}(E)$ is the period of time required for an ion to fly through the ion-accelerating region, $T_{free}(E)$ is the period of time required for the ion to fly through the field-free drift region, and $T_{ref-a}(E)$ and $T_{ref-b}(E)$ are the periods of time required for the ion to fly through the second and first stages of the reflector, respectively. Even in the case of including the ion source, it is possible to analytically determine the second-order focusing condition (a, p) corresponding to equations (2) by imposing the condition for the second-order focusing, i.e. $(dT_{ID}/dE)_{E=1}=0$ and $(d^2T_{ID}/dE^2)_{E=1}=0$, although the result will be much more complex than equations (2). That is to say, when the parameters b, c and d are given, the values of (a, p) which satisfies the second-order focusing condition will be uniquely determined.

Figure 18:
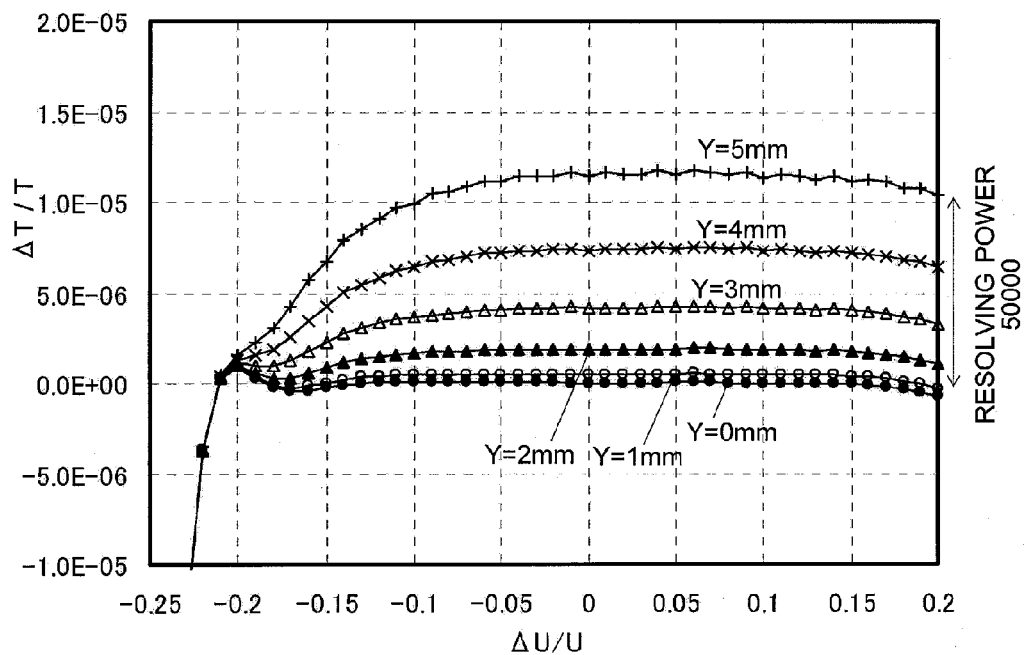
FIG. 18 is a result of a simulation (3D-SIM) performed on the assumption that the grid electrode in the system shown in FIG. 17 is an ideal grid electrode.

When the aforementioned parameter values are used, the second-order focusing condition will be (a, p)=(85.732231, 0.734312). Then, as in the previously described cases, a correcting potential is superposed on the region deeper than the second-order focusing position so as to achieve isochronism for ions with energy $E\geq1$. In the simulation, using equations (19), an ideal correcting potential was calculated, and an appropriate voltage was applied to each guard-ring electrode so as to create an ideal form of the real potential on the central axis of the reflector. FIG. 18 shows the simulation result (3D-SIM) obtained on the assumption that the grid electrode is an ideal grid electrode (which causes neither the seeping of the electric field nor the deflection of ions). There is no dependency of the time of flight on the Y-directional position within the range of $\Delta U/U<-0.2$, since the ions within this range are reflected by the uniform electric field in the region before the second-order focusing position and cannot reach the correcting potential region. On the other hand, within the range of $-0.2\leq\Delta U/U\leq0.2$, where the ions are reflected by the correcting potential region, as the ion trajectory becomes more displaced from the central axis, the mass-resolving power deteriorates as a result of an increase in the temporal aberration due to the off-axis location. Nevertheless, the mass-resolving power of approximately 40,000 to 50,000 can be achieved by merely limiting the ion path within a range of $Y\leq5$ mm from the central axis.

Figure 19:
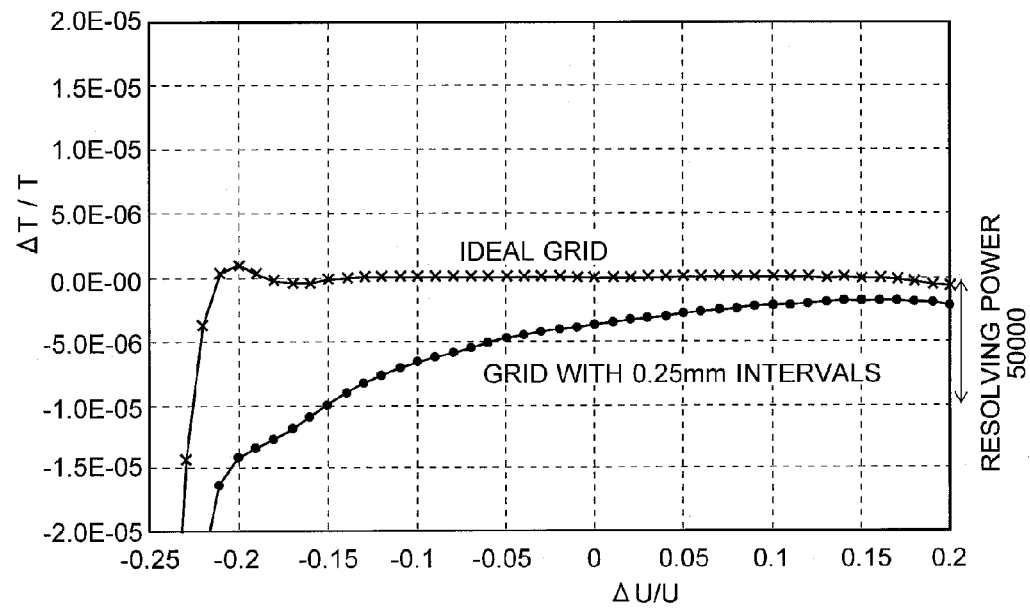
FIG. 19 is a result of a simulation (3D-SIM) for Y=0 in a system using a parallel wire-grid electrode as the boundary of the electric fields.

To investigate an even more realistic case, the simulation has also been performed for a system using a parallel wire-grid electrode (with grid intervals of 0.25 mm) as the grid electrode placed at the boundary of the electric fields in the reflector. The voltage values applied to the guard-ring electrodes were the same as the previous simulation. The simulation result (3D-SIM) at Y=0 is shown in FIG. 19. As shown in this figure, when a parallel wire-grid electrode is used, the isochronism is significantly broken and it is impossible to achieve a high level of mass-resolving power. This is because the second-order focusing condition changes due to the seeping of the electric fields at the grid electrode.

Figure 20:
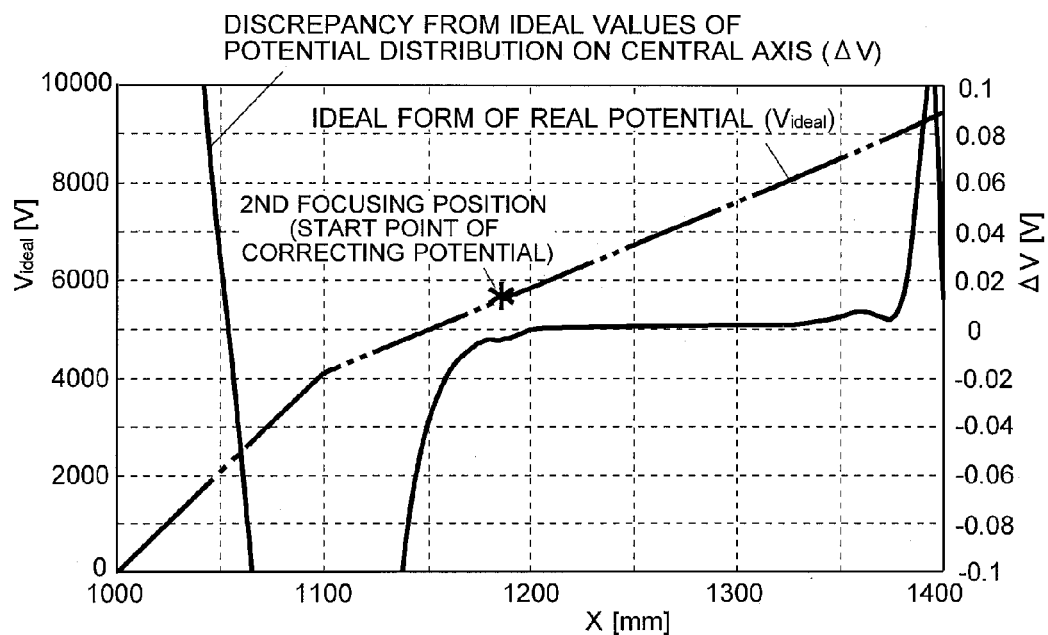
FIG. 20 is a graph showing an ideal form of the real potential (1D-IDL) in a system using a parallel wire-grid electrode as the boundary of the electric fields, and the discrepancy of a corresponding three-dimensional approximate potential distribution (3D-SIM) from the ideal values.

FIG. 20 shows an ideal form of the real potential $V_{ideal}$ and the discrepancy $\Delta V$ from the ideal values of the three-dimensional approximate potential distribution (3D-SIM) corresponding to the ideal form. The graph shows that the formed potential distribution significantly changed due to the seeping of the electric field through the grid electrode. The seeping of the electric field reached close to the starting point of the correcting potential (second-order focusing position), causing the electric field to be non-uniform in the vicinity of the starting point of the correcting potential. This means that, if the reality is taken into consideration, the conventional techniques which assume the presence of a uniform electric field in the vicinity of the starting point of the correcting potential (as in the documents of Cotter et al. or the document of Doroshenko) have limitations. Even the aforementioned practically available fine-mesh grid electrode with grid intervals of 0.25 mm cannot prevent the influence of the seeping of the electric field. This problem will be more serious in the case of the previously mentioned grid-less reflector, because the degree of non-uniformity of the electric field is even greater in the grid-less structure. Accordingly, in practical situations, it is necessary to devise a electric-field correction method that is applicable even if the electric field serving as the base in the vicinity of the starting point of the correcting potential is a non-uniform electric field, so as to satisfy the previously described condition <5: Tolerance for Non-Uniform Electric Field before Correction>.

To address this problem, a method for achieving isochronism even in the case of the non-uniform electric field in which the gradient of the base potential in the vicinity of the starting point of the correcting potential is non-linear is hereinafter considered as an improved version of the previously described method. In the previous descriptions relating to the dual-stage reflector, it was assumed that only a uniform electric field was present in the vicinity of the boundary (the starting point of the correcting potential, or the second-order focusing position) between the first section (before the second-order focusing position) and the second section (after the second-order focusing position) before the correction, and a certain correcting potential was superposed on the base potential created by the uniform electric field in the second section. Actually, as will be explained later, the same method can also be applied in the case where the base potential in the vicinity of the boundary is a non-uniform electric field. That is to say, even if the base potential is a non-uniform electric field, the conclusions deduced on the assumption that a uniform electric field is present also hold true: for example, even in the case of a non-periodic motion, the N-th order focusing position is the best starting point for minimizing the amount of the correcting potential; or even if important components that do not produce periodic motions (e.g. an ion source) are included, complete isochronism for the entire system including such components can be achieved by calculating the N-th order focusing position inside the ion reflector for the entire system and superposing the correcting potential on the region deeper than that position.

Figure 21:
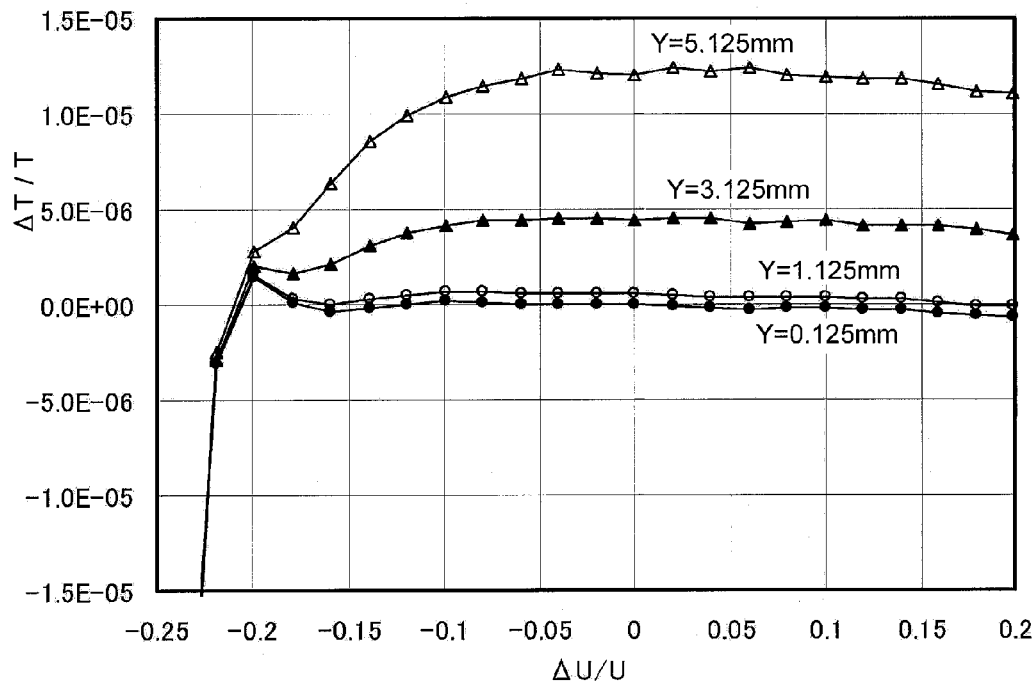
FIG. 21 is a graph showing a result of a simulation (3D-SIM) of the system shown in FIG. 17 using a practical grid electrode and taking into account the seeping of the electric field at the grid electrode.

A specific result is hereinafter demonstrated. As shown in FIG. 20, the potential due to the seeping of the electric field through the grid electrode exponentially changes, and this change must be taken into account when determining the second-order focusing condition over the entire system. Since the equation in this case was too complex to be analytically solved, a numerical computation was performed to solve it. In the present example, the second-order focusing condition was (a, p)=(85.732231, 0.734312) when the seeping of the electric field was not considered, which changed to (a, p)= (85.959433, 0.733742) when the seeping of the electric field was considered. Using the thus obtained new second-order focusing condition and the potential distribution over the entire system, a new correcting potential distribution inside the reflector, i.e. the voltage values applied to the guard-ring electrodes, was calculated. FIG. 21 shows the simulation result (3D-SIM) in the case where the seeping of the electric field at the grid electrode was included. A comparison of the result of FIG. 21 with those of FIG. 18 or 19 demonstrates that a high level of isochronism was restored by the recalculation which took into account the seeping of the electric field.

A method for suppressing the influence of the off-axis aberration is hereinafter described. As shown in FIG. 17, the ion source (orthogonal accelerator section) has a comparatively strong electric field created inside so as to reduce the turn-around time of the ions. The grid electrode placed at the exit of the ion source causes the ion beam to significantly diverge, forming a broadened beam when entering the reflector, which causes deterioration in the mass-resolving power. As stated earlier, there are two methods for reducing the off-axis aberration. The first method is to reduce the second derivative $\Phi''(X)$ of the potential on the central axis. As already described, this can be achieved by using a potential distribution as close to the uniform electric field as possible.

The second method is to reduce the spatial spread of the ion beam in the vicinity of the starting point of the correcting potential. One simple method to achieve this is to place an aperture, slit or similar element for limiting the spread of the ion beam between the reflector and the ion source or elsewhere, or to provide the reflector or an electrode of the ion source with the function of limiting the spread of the ion beam, thus removing (blocking) incident ions significantly displaced from the central axis. The aperture size or slit width should preferably be adjusted depending on the required mass-resolving power and sensitivity; for example, if a high mass-resolving power is needed, the aperture size or slit width can be reduced. Although it decreases the amount of ions and sacrifices the signal intensity, a merit exists in that it improves the mass-resolving power by using only the ion components with smaller temporal aberrations. One possible method for suppressing the influence of the off-axis aberration without sacrificing the amount of ions is to place a focusing lens on the ion path between the ion source (orthogonal accelerator section) and the reflector so as to reduce the spatial spread of the ion beam in the vicinity of the starting point of the correcting potential. Alternatively, it is also possible to provide the ion source with the effect of the focusing lens. By regulating the voltage applied to the focusing lens, the spatial spread of the ions entering the reflector can be reduced, and the divergence of the ion beam or the temporal aberration can be reduced.

[Theoretical Explanation of <5: Tolerance for Non-Uniform Electric Field Before Correction>]

In the previous explanation, the necessity of the previously described <5: Tolerance for Non-Uniform Electric Field before Correction> for the practical realization of an ideal reflectron has been demonstrated based on the simulation results. A rationale for the <5: Tolerance for Non-Uniform Electric Field before Correction> is hereinafter presented.

Initially, the previous explanations relating to the non-periodic motion are reorganized: It is equation (19-3) that is central to the handling of non-periodic motions. Equation (19-3) is the most general equation for deriving the potential distribution $\Delta X_B(U)$ in an arbitrary region (which is hereinafter called the "second section") from the time of flight $T_B(E)$ in that region. The reason is that $T_B(E)$ is merely defined as the time of flight in the second section, and the only condition imposed thereon is that the total time of flight should be exactly equal to the constant value $T(E_0)$. A more specific explanation is as follows: Since the time of flight spent in the first section (including the forward and return paths) is defined as $T_{A-1}(E)$, the equation $T_B(E)=T(E_0)-T_{A-1}(E)$ should hold true when the complete isochronism is achieved. However, $T_{A-1}(E)$ is under no restriction other than that it should physically take a positive value as a function of energy E, and as a result, equation (19-3) will hold true by merely imposing the restriction that $T_B(E)$ should also be a positive value. Actually, by merely replacing $E_0$ with 0 and $X_0$ with 0 in equation (19-3), i.e. by translating the energy and the coordinate origin and assuming a potential distribution which is symmetrical with respect to the line X=0, the equation (8) which is important in the case of periodic motions is once more obtained as a special case.

It is notable that both equation (19-3) and equation (8) which is the corresponding general equation to be used for periodic motions are a definite integral with respect to energy having an integral kernel of $1/\sqrt{\text{const.}-E}$. Therefore, equation (19-3) also satisfies the principle of superposition. That is to say, provided that $\Delta X_{B1}(\alpha)$ and $\Delta X_{B2}(\alpha)$ denote the potential distributions in the second section which respectively correspond to the times of flight $T_{B1}(E)$ and $T_{B2}(E)$ in the second section, when the time of flight in the second section is the sum of the aforementioned times of flight, $\{T_{B1}(E)+T_{B2}(E)\}$, the corresponding potential distribution in the second section will be $\{\Delta X_{B1}(\alpha)+\Delta X_{B2}(\alpha)\}$.

Based on the principle of superposition, the correcting potential, i.e. the discrepancy $\Delta X_B(\alpha)-\Delta X_A(\alpha)$ from the uniform electric field serving as the base potential, can be expanded into a half-integer power series even in the case of a non-periodic motion, as will be hereinafter demonstrated in a reorganized way. This is because the aforementioned condition <5: Tolerance for Non-Uniform Electric Field before Correction> can be derived by reorganizing the discussion.

In equation (19-5), two cases are assumed: In one case, the potential distribution $\Delta X_B(\alpha)$ corresponds to the time of flight $T_B(E)$ in the second section, and the isochronism is achieved over the entire system. In the other case, the same uniform electric field $\Delta X_A(\alpha)$ as used in the first section is also continuously extended into the second section, and a time of flight $T_{A-2}(E)$ in the second section is obtained. Applying the principle of superposition to these two cases naturally leads to the conclusion that, when the difference in the time of flight in the second section is $\{T_B(E)-T_{A-2}(E)\}$, the difference in the potential distribution, i.e. the discrepancy from the uniform electric field creating the base potential in the second section, will be $\{\Delta X_B(\alpha)-\Delta X_A(\alpha)\}$. Equation (19-6) can be obtained by substituting the following equation (20) into equation (19-5).

$$T_B(E)-T_{A-2}(E)=\{T_{A-2}(E)+T_B(E)\}-\{T_{A-1}(E)+T_{A-2}(E)\}=T(E_0)-T_A(E) \tag{20}$$

Equation (20) can be easily derived from the relationship that [total time of flight]=[time of flight in the first section]+[time of flight in the second section], and from the fact that the total time of flight $T(E)=T(E_0)$=constant (because the complete isochronism is assumed). Furthermore, equation (19-7) demonstrates that, when the Taylor expansion in the vicinity of the energy $E_0$ is applied to the difference $T(E_0)-T_A(E)$ in the total time of flight (which is a technique frequently used for multi-stage reflectrons), $T(E_0)-T_A(E)$ will be expressed by the sum of the terms of an integer power series of $(E-E_0)$. Therefore, even in the case of the non-periodic motion, the conclusion is reached that imposing the N-th order focusing condition makes $T(E_0)-T_A(E)$ smaller in the vicinity of the energy $E_0$ and naturally causes $\Delta X_B(\alpha)-\Delta X_A(\alpha)$ to be smaller, as in the case of the periodic motion.

The following equation (21) specifically shows an expanded expression of the correcting potential $\Delta X_B(\alpha)-\Delta X_A(\alpha)$ obtained by actually substituting equation (19-7) into equation (19-6).

$$\sqrt{2}\pi \cdot \{\Delta X_B(\alpha) - \Delta X_A(\alpha)\} = \int_{E_0}^{\alpha} dE \frac{1}{\sqrt{\alpha - E}} \tag{21}$$

$$\left[-\frac{1}{1!}(dT_A/dE)(E-E_0)^1 - \right.$$

$$\frac{1}{2!}(d^2T_A/dE^2)(E-E_0)^2 -$$

-continued $$\frac{1}{3!}(d^3 T_A/dE^3)(E-E_0)^3 - \ldots \Big]$$

$$= -\int_{E_0}^{\alpha} dE \frac{(dT_A/dE)(E-E_0)}{1!\sqrt{\alpha-E}} -$$

$$\int_{E_0}^{\alpha} dE \frac{(d^2 T_A/dE^2)(E-E_0)^2}{2!\sqrt{\alpha-E}} -$$

$$\int_{E_0}^{\alpha} dE \frac{(d^3 T_A/dE^3)(E-E_0)^3}{3!\sqrt{\alpha-E}} - \ldots$$

$$= \frac{1}{1!}\frac{2}{1}\frac{2}{3}(dT_A/dE)(\alpha-E_0)^{3/2} -$$

$$\frac{1}{2!}\frac{2}{1}\frac{2}{3}\frac{2}{5}(d^2 T_A/dE^2)(\alpha-E_0)^{5/2} -$$

$$\frac{1}{3!}\frac{2}{1}\frac{2}{3}\frac{2}{5}\frac{2}{7}(d^3 T_A/dE^3)(\alpha-E_0)^{7/2} - \ldots$$

In this equation, $(d^N T_A/dE^N)$ is the N-th order differential coefficient (where N=1, 2, 3, ... ) obtained by expanding the total time of flight $T_A(E)$ in the base potential created by a uniform electric field into a Taylor series in the vicinity of the energy $E_0$ at the starting point of the correcting potential. Equation (21) shows that the discrepancy $\Delta X_B(\alpha) - \Delta X_A(\alpha)$ from the uniform electric field can be expressed by a half-integer power series of $(\alpha - E_0)^{(N+1/2)}$, and the expansion coefficient of the (N+½)-th power is proportional to the N-th order derivative value $a_N$. In other words, if the starting point of the correcting potential is at the N-th order focusing position, then $a_1 = a_2 = \ldots = a_N = 0$, so that the half-integer power series can naturally be approximated by the (N+3/2)-th power of $(\alpha - E_0)$. In summary, even in the case of the non-periodic motion, the correcting potential can be expressed by a half-integer power series, as in the case of the periodic motion, by expanding the entire integral into a Taylor series and processing each of the thereby obtained terms based on the principle of superposition.

The same conclusion can be derived even if the base potential $\Delta X_A(\alpha)$ before the application of the correcting potential is not a uniform electric field (i.e. if it is a non-uniform electric field), as will be hereinafter described. Equation (19-5) has been derived from the principle of superposition and hence holds true even if $\Delta X_A(\alpha)$ is not a uniform electric field. Equation (19-6) has been obtained by substituting an obvious relational expression relating to the time of flight, i.e. $T_B(E) - T_{A\text{-}2}(E) = T(E_0) - T_A(E)$, into equation (19-5) and therefore holds true even if $\Delta X_A(\alpha)$ is not a uniform electric field. Equation (19-7) holds true if the difference $T(E_0) - T_A(E)$ in the total time of flight can be expanded into a Taylor series. This constraint condition will also be satisfied if $\Delta X_A(\alpha)$ is a function that is smoothly connected at the starting point of the correcting potential (i.e. that is infinitely differentiable), even if the electric field is not uniform. Actually, when a potential distribution created in a vacuum area by using thin-plate aperture electrodes or similar electrodes as the guard-ring electrodes is used as the base potential, the aforementioned constraint condition is automatically satisfied. This is because such a potential distribution is a solution of the Laplace equation, which is theoretically known to be a smooth function that is infinitely differentiable with respect to a spatial coordinate in a vacuum area where there is no guard-ring electrode or grid electrode and hence no electric charge. (For example, refer to the description of the Newton potential and the subsequent theorem No. 2 in "§87 Poisson Houteishiki (Poisson Equations)" of Kousaku Yoshida, *Bibun Houteishiki No Kaihou, Dai 2 Han* (*Solution of Differential Equations, 2nd Edition*), Iwanami Zensho).

In summary, if an arbitrary potential distribution in a vacuum area that satisfies the Laplace equation (which may naturally include a non-uniform electric field) is used as the base potential $\Delta X_A(\alpha)$, the two important conclusions can be derived as in the case of the uniform electric field; i.e. firstly, the correcting potential can be expanded into a half-integer power series, and secondly, a correcting potential with the N-th order focusing position as the starting point of the correcting potential can be approximated by the (N+3/2)-th power. This is the very rationale for the fact that the condition <5: Tolerance for Non-Uniform Electric Field before Correction> is satisfied.

[Distinction Between Base Potential and Correcting Potential]

One method for distinguishing the contributions of the base potential $X_A(U)$ and the correcting potential $X_C(U)$ for a given real potential $X_R(U)$ created along the central axis of the reflector is subsequently described. The hereinafter described method can be used even if both the base potential $X_A(U)$ and the correcting potential $X_C(U)$ are created by non-uniform electric fields. The method is also applicable in the case where the seeping of the electric field occurs at the grid electrode, or in the case where no grid electrode is used.

Suppose that a real potential $X_R(U)$ has been revealed as shown in FIG. 25A. If $X_R(U) = X_A(U) + X_C(U)$ is numerically differentiated and $d^{N+2} X_R/dU^{N+2}$ is examined, a specific peak appears at $U = E_0$, as shown in FIG. 25B. By contrast, no such specific peak can be found at $dX_R/dU$, $d^2 X_R/dU^2$, ..., and $d^{N+1} X_R/dU^{N+1}$. These results suggest that $X = X_0$ is the N-th order focusing position. The reason for this conclusion is that, in the differential of the sum $(d^{N+2} X_R/dU^{N+2}) = (d^{N+2} X_A/dU^{N+2}) + (d^{N+2} X_C/dU^{N+2})$, the first term on the right side will not diverge, however many times it is differentiated, whereas the second term on the right side does not diverge up to the (N+1)-st order differential but changes to divergence in the (N+2)-nd order differential.

As one example, the case of N=2 is hereinafter described with reference to FIGS. 10A and 10B. The base potential $X_A(U)$ in FIG. 10A is assumed to be a uniform electric field, although a non-uniform electric field may be used as the base potential $X_A(U)$.

First, the total time of flight T(E) for energy E is determined. This is the "total time of flight due to real potential" shown by the solid line in FIG. 10B. Under ideal conditions, the time of flight in $E \geq E_0$ will be constant. Next, the total time of flight $T_D(E)$ due to the base potential in $E \geq E_0$ is determined by extrapolation from the functional form in $E < E_0$. This can be determined from the condition that the differential coefficients of the time of flight with respect to the energy at the second-order focusing point $E = E_0$ are continuous up to an infinitely high-order term. That is to say, the functional form of $T_D(E)$ in $E \geq E_0$ can be estimated by using the differential coefficients as approached from the lower-energy side: $(dT/dE)_{E \to E_0-}$, $(d^2 T/dE^2)_{E \to E_0-}$, $(d^3 T/dE^3)_{E \to E_0-}$, .... Subsequently, the correcting potential $X_C(U)$ is determined by substituting $T_D(E_0) - T_D(E)$ into the right side of equation (13-3). Furthermore, the base potential $X_A(U)$ can be determined by subtracting the correcting potential $X_C(U)$ from the real potential $X_R(U)$.

[TOFMS as One Embodiment of Present Invention]

Figure 22:
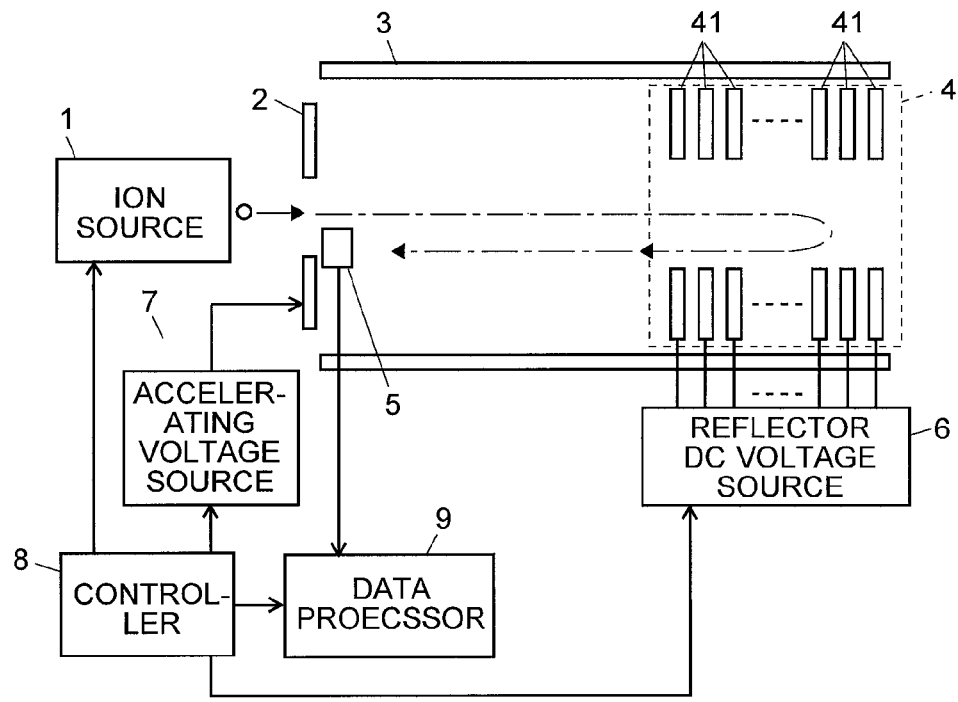
FIG. 22 is a schematic configuration diagram of a TOFMS according to one embodiment of the present invention.

A time-of-flight mass spectrometer (TOFMS) as one embodiment of the present invention having the previously described characteristic ion reflector is hereinafter described. FIG. 22 is a schematic configuration diagram of the TOFMS of the present embodiment.

In FIG. 22, the ions originating from a sample produced in an ion source 1 (which corresponds to the ion ejector in the present invention) are given an amount of initial energy from an electric field created by a voltage applied to an accelerating electrode 2 from an accelerating voltage source 7, to be injected into a flight space formed within a flight tube 3. The flight tube 3 contains an ion reflector 4 consisting of a plurality of guard-ring electrodes 41 arranged along an ion beam axis. Each ion is reflected by an electric field created by the ion reflector 4. The reflected ions fly backward and arrive at a detector 5, which produces a detection signal corresponding to the amount of incoming ions.

A reflector DC voltage source 6 (which corresponds to the reflector driver in the present invention) applies a predetermined voltage to each of the guard-ring electrodes 41 constituting the ion reflector 4, whereby an electrostatic field (DC electric field) having a predetermined potential distribution is created within the space inside the ion reflector 4. The ion source 1, accelerating voltage source 7, reflector DC voltage source 6 and other components are controlled by a controller 8. A data processor 9 receives information about the timing of accelerating ions, i.e. information about the time of departure of the ions, from the controller 8. With reference to this information, it measures the time of flight of each ion based on the detection signal of the ion, and converts the times of flight into mass-to-charge ratios m/z to create a mass spectrum.

For example, the ion source 1 may be a MALDI ion source. Alternatively, an atmospheric pressure ion source, such as an ESI (electrospray ionization) or APCI (atmospheric pressure chemical ionization), may be used for liquid samples, or an EI (electron ionization) or CI (chemical ionization) ion source may be used for gas samples. In these alternative cases, an ion trap may preferably be provided instead of the ion source 1, in which case the ions are temporarily captured in the ion trap and subsequently ejected toward the flight tube 3. To suppress the variation in the initial energy of the ions, it is preferable to create an accelerating electric field so that the ions extracted from the ion source 1 are accelerated toward and injected into the flight tube 3 in a direction orthogonal to the extracting direction of the ions.

In the TOFMS of the previously described embodiment, the DC voltages $V_1, V_2, \ldots, V_n$ applied from the reflector DC voltage source 6 to the guard-ring electrodes 41 are respectively set at values which have been predetermined so as to create, within the space surrounded by the guard-ring electrodes 41, a potential in which a uniform electric field extends up to the N-th order focusing position on the flight path of the ions while a predetermined correcting potential is superposed on the uniform electric field in the region deeper than the N-th order focusing position. As already explained, the voltages to be applied to the guard-ring electrodes 41 of the ion reflector 4 and the thereby created potential distribution can be determined by simulation calculations. Therefore, once the desired potential distribution is fixed in the previously described manner, the voltage values for realizing the potential distribution can be determined beforehand (in the system design phase) by calculations.

The guard-ring electrodes 41 constituting the ion reflector 4 only need to form a structure which surrounds one space in its entirety, and there are some degrees of freedom in terms of specific forms. For example, the opening shape of the electrodes as viewed along the central axis C of the ion reflector 4, which is circular in the previous example, may alternatively be shaped like an ellipse, tetragon, polygon, slit or any other form. Each guard-ring electrode may be composed of a plurality of electrode segments.

Instead of individually applying voltages from the reflector DC voltage source 6 to the guard-ring electrodes 41, it is possible to divide one voltage by resistors and apply one fraction of the voltage to each of the guard-ring electrodes 41. Naturally, in this case, the voltages applied to the guard-ring electrodes 41 can be adjusted by regulating the resistance values of the network resistor used for the resistive division. It is also possible to construct the electrode as a resistive body having a tubular or similar shape whose electric resistance along the ion beam axis can be adjusted so as to create the previously described potential inside. Another example is a reflector composed of a plurality of printed circuit boards each of which has a group of electrodes formed by an etching or similar process and which are arranged so as to surround a space within which a reflecting electric field is to be created.

The incident direction of the ions into the ion reflector 4 may be parallel to the central axis C so that both forward and return paths of the ions lie on approximately the same line, as shown in FIG. 22. It is also possible to inject ions at an angle to the central axis C so that the forward and return paths of the ions will not overlap each other, as shown in FIG. 17.

As described previously, in the TOFMS according to the present invention, complete isochronism can be realized by appropriately setting the electric fields created by the ion reflector even if a component that does not produce a periodic motion is included. Therefore, it is possible to provide an ion optical element between the ion reflector 4 and the ion source 1 or the detector 5 (i.e. within the field-free drift region) inside the flight tube 3, such as an ion lens for converging ions, an accelerator or decelerator for increasing or decreasing the speed of ions by an electric or magnetic field, or a deflector for bending the trajectory of ions.

The TOFMS in the previous embodiment detects ions after making them fly back and forth by the previously described characteristic ion reflector. Instead of such a simple reflection type, a multi-reflection TOFMS may be constructed by placing two sets of the previously described ion reflectors across the field-free drift region so as to make ions fly back and forth a plurality of times between the ion reflectors.

In the dual-stage reflectron described in the previous embodiment, the starting point of the correcting potential was set at the second-order focusing position, using the second-order focusing condition. However, it is also possible to use the first-order focusing condition in the dual-stage reflectron and set the starting point of the correcting potential at the first-order focusing position.

When the second-order focusing condition is imposed, (a, p) will be uniquely determined from equation (2), whereas, when the first-order focusing condition is imposed, a relational expression of a and p is obtained and there are an infinite number of solutions (a, p). This suggests that, when the first-order focusing condition is used, the first-order focusing position can be set at any position. When the first-order condition is used, the correcting potential in the vicinity of the starting point of the correcting potential is approximated by the $2.5^{th}$ power, and the discrepancy from the ideal values (1D-IDL) of the potential created in the vicinity of the starting point of the correcting potential is greater than in the case where the second-order focusing condition is satisfied. Therefore, the best performance cannot be achieved. Nevertheless, the system is adequate for practical uses, as already stated in the embodiment of the single-stage reflectron. Naturally, the performance can be improved by bringing the first-order focusing position closer to the second-order focusing position. In particular, even in the case of the first-order focusing, if the first-order focusing position is set within the previously described range of the second-order focusing position, the performance will be almost as high as in the case of the second-order focusing.

To put it generally, in a multi-stage ion reflector having M stages, if the N-th order focusing position (N≤M; N=1, 2, . . . ) inside the ion reflector is selected as the starting point of the correcting potential superposed on the deeper region, and if the correcting potential is proportional to $\{U(X)-E_0\}^{N+3/2}$ in the vicinity of the boundary of the starting point, the system falls within the scope of claims of the present patent application.

Although a multi-stage reflector was described as a reference model in the previous embodiment, the TOFMS according to the present invention is totally independent of the form of the reflector, such as the number of stages or the presence of a grid electrode. That is to say, the characteristics of the TOFMS according to the present invention as defined in the scope of claims of the present patent application can be summarized as follows.

As a preparatory phase for the superposition of a correcting potential for achieving complete isochronism, a virtual reflectron which approximately achieves isochronism based on a conventional technique and can serve as a base is considered. This reflectron serving as a base should satisfy the following three conditions:

(i) There is no restriction on the form of the reflector, such as the number of stages or the presence of a grid electrode.

(ii) The reflector only needs to have an inner hollow space with a monotonously changing gradient potential for reflecting ions (a monotonously increasing potential if the target is a positive ion, or a monotonously decreasing potential if the target is a negative ion). It does not matter whether the gradient potential is created by a uniform or non-uniform electric field.

(iii) The system is tuned to satisfy the M-th order focusing condition, so as to ensure a certain range of energy where the energy focusing is achieved (i.e. the time of flight is independent of the initial energy). For example, as explained in the previous embodiment, the first-order focusing condition is used for the Wiley-McLaren solution, the second-order focusing condition for the Mamyrin solution, and so on. As an extension of this condition, it is possible to say that, in the case of an M-stage reflector, the system can be tuned so as to satisfy the focusing condition of up to the M-th order. In the case of a reflectron having a grid-less structure, unlike the multi-stage reflectron, the focusing condition cannot be analytically determined. However, it is still possible to determine the M-th order focusing condition by numerical calculations or other methods. To put it generally, in the reflectron which is to be used as the base, the M-th order focusing condition is determined by analytical or numerical calculations and the result is used for the energy focusing.

In the TOFMS according to the present invention including the aforementioned ion reflector which satisfies the M-th order focusing condition and serves as the base, the N-th order focusing position in the ion reflector is chosen as the starting point of the correcting potential (N≤M; N=1, 2, . . . ), and a correcting potential which follows a function that is approximated by a (N+½)-th power in the vicinity of the starting point and smoothly extended from the starting point into the deeper region is superposed on the potential serving as the base. As a result, isochronism is achieved for ions reflected in an area deeper than the starting point of the correcting potential (the N-th order focusing position), the divergence of the ion beam and the off-axis aberration are suppressed to the minimum, and furthermore, the potentials before and after the starting point of the correcting potential are smoothly connected. As noted earlier, this technique can also be applied in the case of handling a non-periodic motion including the ion source.

It should be noted that any change, modification or addition appropriately made within the spirit of the present invention in various respects other than the previously described ones will evidently fall within the scope of claims of the present patent application.

| EXPLANATION OF NUMERALS | |
|---|---|
| 1 | Ion Source |
| 2 | Accelerating Electrode |
| 3 | Flight Tube |
| 4 | Ion Reflector |
| 41 | Guard-Ring Electrode |
| 5 | Detector |
| 6 | Reflector DC Voltage Source |
| 7 | Accelerating Voltage Source |
| 8 | Controller |
| 9 | Data Processor |

The invention claimed is:

1. A time-of-flight mass spectrometer including an ion ejector for accelerating target ions by imparting a certain amount of energy to the ions, an ion reflector for reflecting ions ejected from the ion ejector and turning the ions around by an effect of an electric field, an ion detector for detecting the ions reflected by and exiting from the ion reflector, and a reflector driver for driving the ion reflector so as to create a reflecting electric field inside the ion reflector, wherein:

with X denoting a coordinate along a central axis of the ion reflector, the reflector driver applies a voltage to the ion reflector so as to create, inside an inner hollow area of the ion reflector and along the central axis of the ion reflector, a predetermined potential distribution $U_A(X)$ in which the potential monotonously changes over the entire ion reflector and therefore an inverse function $X_A(U)$ can be uniquely obtained, thus creating an N-th order focusing position at a position with coordinate $X_0$ and potential $E_0$ inside the ion reflector; and the reflector driver also applies a voltage to the ion reflector within a space having the N-th order focusing position with coordinate $X_0$ as a starting point and extending into a deeper region, so as to superpose, on the predetermined potential $X_A(U)$, a predetermined correcting potential $X_C(U)$ which can be approximated by a formula proportional to $\{U(X)-E_0\}^{N+3/2}$ in a vicinity of the coordinate $X_0$ and which is expressed as a smooth function continuing from the coordinate $X_0$ into the deeper region.

2. The time-of-flight mass spectrometer according to claim 1, wherein:

a forward ion drift region for making the ions ejected from the ion ejector fly forward is provided between the ion ejector and the ion reflector, the ion reflector subsequently reflects the ions passing through the forward ion drift region and turns the ions around by the effect of the electric field; and a backward ion drift region for making the ions reflected by and exiting from the ion reflector fly in a direction opposite to the forward ion drift region is provided between the ion reflector and the ion detector.

3. The time-of-flight mass spectrometer according to claim 1, wherein:

either the ion ejector and the ion reflector, or the ion reflector and the ion detector, or both are connected to each other with no drift region or similar space provided in between.

4. The time-of-flight mass spectrometer according to claim 1, wherein:
the electric field which is to be the predetermined potential distribution $X_A(U)$ is a uniform electric field at least in a vicinity of the coordinate $X_0$.

5. The time-of-flight mass spectrometer according to claim 1, wherein:
a grid electrode is provided inside an inner hollow area of the ion reflector, the grid electrode dividing the ion reflector into a plurality of stages.

6. The time-of-flight mass spectrometer according to claim 1, wherein:
a grid-less structure with no grid electrode provided inside an inner hollow area of the ion reflector is adopted.

7. The time-of-flight mass spectrometer according to claim 1, wherein:
the ion reflector is a single-stage system, a first-order focusing position inside the ion reflector is selected as the starting point, and a correcting potential for N=1, which is proportional to $\{U(X)-E_0\}^{2.5}$, is superposed on a region in a vicinity of a boundary of the starting point.

8. The time-of-flight mass spectrometer according to claim 1, wherein:
the ion reflector is a dual-stage system, a second-order focusing position inside the ion reflector is selected as the starting point, and a correcting potential for N=2, which is proportional to $\{U(X)-E_0\}^{3.5}$, is superposed on a region in a vicinity of a boundary of the starting point.

9. The time-of-flight mass spectrometer according to claim 1, wherein:
the ion reflector is a dual-stage system, a first-order focusing position inside the ion reflector is selected as the starting point, and a correcting potential for N=1, which is proportional to $\{U(X)-E_0\}^{2.5}$, is superposed on a region in a vicinity of a boundary of the starting point.

10. The time-of-flight mass spectrometer according to claim 1, wherein:
the ion ejector is an orthogonal acceleration type.

11. The time-of-flight mass spectrometer according to claim 1, wherein:
the ion ejector is a MALDI ion source.

12. The time-of-flight mass spectrometer according to claim 2, wherein:
an accelerating or decelerating region is provided in a portion of the forward ion drift region and/or the backward ion drift region.

13. The time-of-flight mass spectrometer according to claim 2, wherein:
a focusing lens is provided in a portion of the forward ion drift region.

14. The time-of-flight mass spectrometer according to claim 1, wherein:
The ion ejector has a function of a focusing lens.

15. The time-of-flight mass spectrometer according to claim 1, wherein:
an aperture or slit for limiting a passing area of the ions is provided between the ion ejector and the ion reflector.

16. The time-of-flight mass spectrometer according to claim 1, wherein:
the ion ejector or a portion of electrodes of the ion reflector has the function of limiting a passing area of the ions.

17. The time-of-flight mass spectrometer according to claim 1, wherein:
the ion reflector includes a plurality of thin electrodes arranged along an ion beam axis.

18. The time-of-flight mass spectrometer according to claim 1, wherein:
the ion reflector includes a resistance element having an electric resistance adjusted along the ion beam axis.

19. The time-of-flight mass spectrometer according to claim 1, wherein:
the ion reflector is constructed by using a printed circuit board or a microfabricated substrate.

20. The time-of-flight mass spectrometer according to claim 1, which is designed as a multi-reflection time-of-flight mass spectrometer including a plurality of ion reflectors arranged opposite to each other so that ions are reflected a plurality of times between the plurality of ion reflectors, wherein:
at least one of the plurality of ion reflectors is the aforementioned ion reflector in which a predetermined correcting potential $X_C(U)$ is superposed on the predetermined potential $X_A(U)$.

* * * * *